(12) United States Patent
Jamieson et al.

(10) Patent No.: US 11,021,658 B2
(45) Date of Patent: Jun. 1, 2021

(54) METHOD AND FEEDSTOCK FOR PRODUCING HYDROCARBONS

(71) Applicant: Neste Oyj, Espoo (FI)

(72) Inventors: John Jamieson, Porvoo (FI); Antti Ojala, Porvoo (FI)

(73) Assignee: NESTE OYJ, Espoo (FI)

( * ) Notice: Subject to any disclaimer, the term of this patent is extended or adjusted under 35 U.S.C. 154(b) by 0 days.

(21) Appl. No.: 16/944,776

(22) Filed: Jul. 31, 2020

(65) Prior Publication Data

US 2020/0362249 A1 Nov. 19, 2020

Related U.S. Application Data

(62) Division of application No. 16/720,901, filed on Dec. 19, 2019, now Pat. No. 10,844,288.

(30) Foreign Application Priority Data

Apr. 3, 2019 (FI) ...................................... 20195271

(51) Int. Cl.
| | | |
|---|---|---|
| C10G 69/00 | (2006.01) | |
| C10G 9/00 | (2006.01) | |
| C10G 9/32 | (2006.01) | |
| C10G 55/04 | (2006.01) | |
| C07C 7/00 | (2006.01) | |
| C07C 4/04 | (2006.01) | |
| C08F 10/02 | (2006.01) | |
| C08F 10/06 | (2006.01) | |

(52) U.S. Cl.
CPC .................. *C10G 9/32* (2013.01); *C07C 4/04* (2013.01); *C07C 7/00* (2013.01); *C08F 10/02* (2013.01); *C08F 10/06* (2013.01); *C10G 55/04* (2013.01); *C10G 2300/1014* (2013.01); *C10G 2300/1044* (2013.01); *C10G 2300/1081* (2013.01); *C10G 2300/201* (2013.01); *C10G 2300/202* (2013.01); *C10G 2300/207* (2013.01)

(58) Field of Classification Search
CPC .......... C10G 9/00; C10G 69/00; C10G 57/00; C07C 7/00
See application file for complete search history.

(56) References Cited

U.S. PATENT DOCUMENTS

| | | | | |
|---|---|---|---|---|
| 3,944,481 A * | 3/1976 | Wing | ...................... | C10G 69/06 585/651 |
| 4,247,386 A * | 1/1981 | LaPierre | ................. | C10G 47/16 208/111.25 |
| 6,407,301 B1 * | 6/2002 | Foley | ...................... | C10G 25/00 585/650 |
| 7,838,712 B2 * | 11/2010 | Bouvart | ................... | C10G 9/00 585/648 |
| 9,302,960 B2 * | 4/2016 | Lapinski | ................. | C10G 45/58 |
| 9,469,583 B2 * | 10/2016 | Aalto | ........................ | A61K 8/31 |
| 2010/0331502 A1 | 12/2010 | Hecker et al. | | |
| 2011/0230632 A1 | 9/2011 | Abhari | | |
| 2011/0245556 A1 * | 10/2011 | Sohn | ........................ | C10G 63/08 585/300 |
| 2011/0319683 A1 | 12/2011 | Abhari et al. | | |
| 2013/0109893 A1 | 5/2013 | Robota et al. | | |
| 2014/0303057 A1 | 10/2014 | Abhari et al. | | |
| 2017/0298280 A1 * | 10/2017 | Vermeiren | ................ | C07C 4/04 |
| 2018/0179458 A1 * | 6/2018 | Hakola | ................ | C10G 69/126 |
| 2018/0282632 A1 * | 10/2018 | Hakola | ................ | C10G 69/126 |

FOREIGN PATENT DOCUMENTS

| | | |
|---|---|---|
| DE | 20 2010 003894 U1 | 8/2010 |
| EP | 2679656 A1 | 1/2014 |
| EP | 3095843 A1 | 11/2016 |
| EP | 3095844 A1 | 11/2016 |
| FR | 2834515 A1 | 7/2003 |
| WO | 03048087 A1 | 6/2003 |
| WO | 2014111598 A2 | 7/2014 |
| WO | 2015101837 A2 | 7/2015 |
| WO | 2016023973 A1 | 2/2016 |
| WO | 2016058953 A1 | 4/2016 |
| WO | 2018078023 A1 | 5/2018 |
| WO | 2019197721 A1 | 10/2019 |

OTHER PUBLICATIONS

Beens et al., "Comprehensive two-dimensional gas chromatography—a powerful and versatile technique", The Royal Society of Chemistry 2005, pp. 122-127.
Finnish Search Report dated Jul. 8, 2019.
International Search Report (Form PCT/ISA/210) dated Mar. 4, 2020, International Bureau of WIPO, in corresponding International Application No. PCT/FI2019/050909. (5 pages).
International Search Report dated Jan. 30, 2020, by the Finnish Patent Office in corresponding Finnish Application No. 20195906. (1 page).
K. Sinthavarayan, "Masters Thesis, Fractionation and Characterization of Renewable Paraffinic Solvents", Aalto University School of Chemical Technology, Aug. 1, 2013. (91 pages).
Office Action dated Feb. 4, 2020, by the Dutch Patent Office in corresponding Dutch Patent Application No. 2024522. (8 pages).
Office Action dated Jun. 2, 2020, by the Swedish Patent Office in corresponding Swedish Patent Application No. 1951503-0, and an English Translation of the Office Action. (8 pages).
Van Geem et al., "On-line analysis of complex hydrocarbon mixtures using comprehensive two-dimensional gas chromatography", Journal of Chromatography A, 2010, pp. 6623-6633.
Office Action dated Jul. 23, 2020, by the Austrian Patent Office in corresponding Austrian Patent Application No. A51129/2019, and an English Translation of the Office Action. (6 pages).
International type Search Report and Written Opinion by the European Patent Office completed on Jun. 18, 2020 in corresponding Belgian National Application No. BE2019/05942. (13 pages).

(Continued)

*Primary Examiner* — Rip A Lee

(74) *Attorney, Agent, or Firm* — Buchanan Ingersoll & Rooney PC

(57) ABSTRACT

A method for producing a cracking product having a mixture of hydrocarbons, a thermal cracking feedstock, a cracking product containing a mixture of hydrocarbons is disclosed as is a method involving use of the cracking product for producing polymers.

24 Claims, 1 Drawing Sheet

(56) References Cited

OTHER PUBLICATIONS

Anonymous: "2-Methyltetradecane C15H32 ChemSpider", Jan. 23, 2020, XP055781246, Extrait de I'Internet: URL:http://web.archive.org/web/20200123143656/http://www.chemspider.com/Chemical-Structure.14533.html [extrait le Mar. 1, 2021].
International-type Research Report and Written Opinion (Form PCT/ISA/201) dated Mar. 3, 2021, by the International Bureau of European Patent Office in corresponding International Application No. BE 202005751. (10 pages).

* cited by examiner

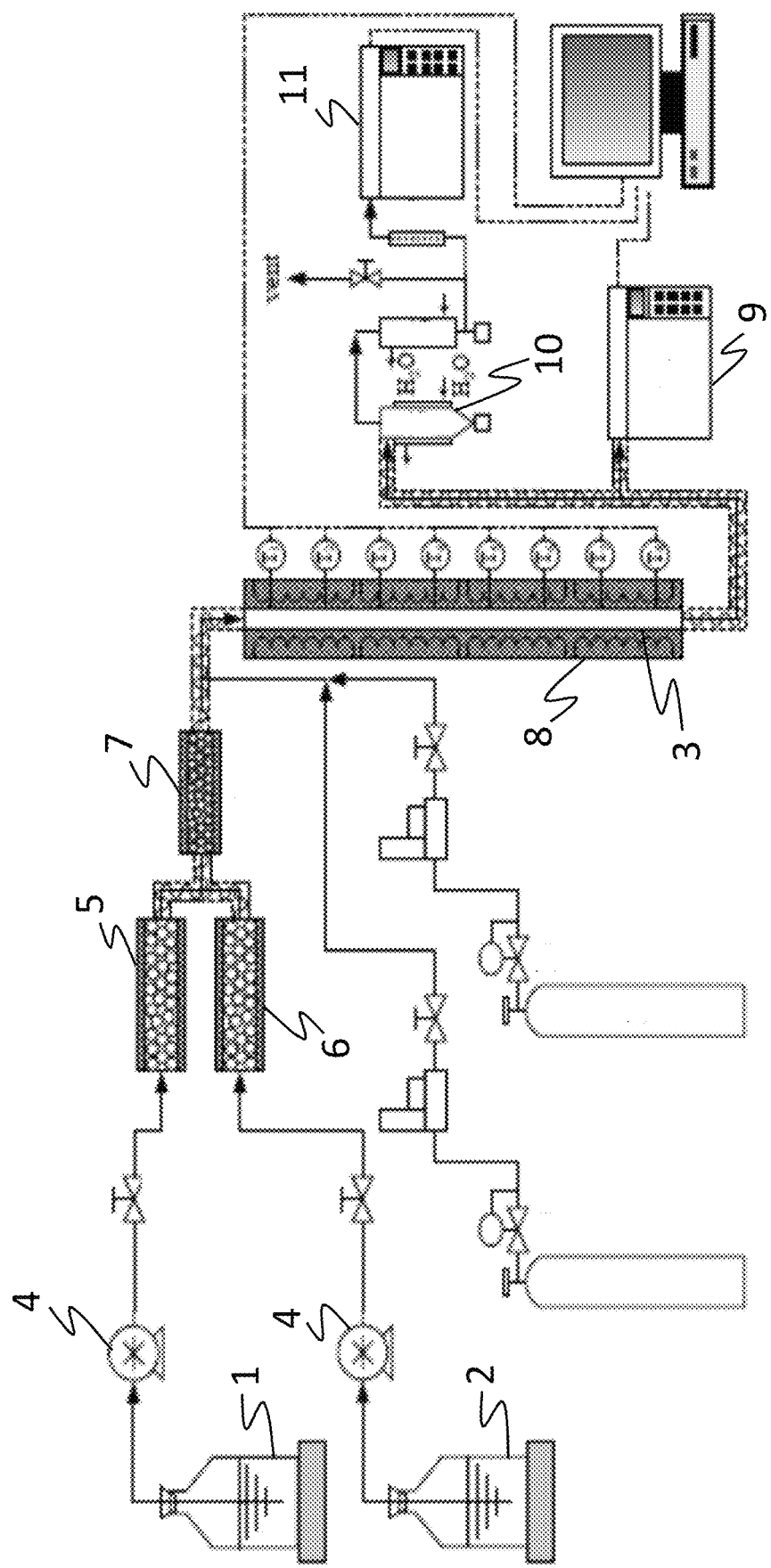

METHOD AND FEEDSTOCK FOR PRODUCING HYDROCARBONS

CROSS REFERENCE TO RELATED APPLICATIONS

This application is a divisional of U.S. application Ser. No. 16/720,901 filed on Dec. 19, 2019, now issued as U.S. Pat. No. 10,844,288, which claims priority to Finnish Application No. 20195271 filed on Apr. 3, 2019.

TECHNICAL FIELD

The present invention generally relates to a method for producing hydrocarbons by thermal cracking. The invention relates particularly, though not exclusively, to a method for producing a cracking product comprising hydrocarbons by thermally cracking a feedstock at least partially derived from renewable sources, and preferably using at least a portion of said cracking product for producing polymers.

BACKGROUND ART

This section illustrates useful background information without admission of any technique described herein representative of the state of the art.

Steam cracking is an important method for producing chemicals from fossil hydrocarbons. Examples of valuable products of a high severity fossil naphtha cracker are ethene, propene, 1,3-butadiene and BTX (benzene, toluene, xylenes). Steam cracking is the main source of raw materials for conventional petrochemistry, and in particular for polymer industry. Major polymers such as polyethene (PE), polypropene (PP), and polyethylene terephthalate (PET) are conventionally obtained from raw materials produced by steam cracking fossil hydrocarbons. Recently, it has been suggested to replace at least a portion of the fossil raw materials conventionally used as steam cracker feedstock with more sustainable raw materials derived from renewable sources to address environmental concerns.

Steam cracking mainly produces hydrocarbons, but for example CO and $CO_2$ are produced as by-products.

SUMMARY

According to a first aspect of the invention there is provided a method comprising the steps of a) providing a thermal cracking feedstock comprising 1-100 wt-% renewable isomeric paraffin composition of the total weight of the thermal cracking feedstock, the renewable isomeric paraffin composition comprising at least 60 wt-% paraffins of the total weight of the renewable isomeric paraffin composition, wherein of said paraffins 10-95 wt-% are isoparaffins, and the ratio of the wt-% amount of isoparaffins with more than three branches to the total wt-% amount of the isoparaffins is less than 0.15, and 0-99 wt-% fossil naphtha of the total weight of the thermal cracking feedstock, the sum of the wt-% amounts of the renewable isomeric paraffin composition and of the fossil naphtha being at least 90 wt-% of the total weight of the thermal cracking feedstock; and b) thermally cracking the thermal cracking feedstock provided in step a) to form a cracking product comprising a mixture of hydrocarbons. The total amount of CO, $CO_2$, and $C_2H_2$ formed in the cracking step is less when thermally cracking a thermal cracking feedstock comprising a renewable isomeric paraffin composition wherein the ratio of the wt-% amount of isoparaffins with more than three branches to the total wt-% amount of the isoparaffins in the renewable isomeric paraffin composition is less than 0.15 compared to thermally cracking a thermal cracking feedstock comprising a renewable paraffin compositions not fulfilling said criterion.

In certain embodiments, the thermal cracking feedstock comprises 50-100 wt-% renewable isomeric paraffin composition of the total weight of the thermal cracking feedstock, and 0-50 wt-% fossil naphtha of the total weight of the thermal cracking feedstock. In certain embodiments, the thermal cracking feedstock comprises 50-85 wt-% renewable isomeric paraffin composition and 15-50 wt-% fossil naphtha, preferably 60-85 wt-% renewable isomeric paraffin composition and 15-40 wt-% fossil naphtha, more preferably 70-85 wt-% renewable isomeric paraffin composition and 15-30 wt-% fossil naphtha, of the total weight of the thermal cracking feedstock. The renewable isomeric paraffin composition promotes formation of high value chemicals (ethene, propene, 1,3-butadiene, benzene, toluene, and xylenes) in the thermal cracking step compared to thermally cracking fossil naphtha. This effect becomes more pronounced as the wt-% amount of the renewable isomeric paraffin composition in the thermal cracking feedstock increases and accordingly, a thermal cracking feedstock comprising at least 50 wt-% of the renewable isomeric paraffin composition is preferred. Increasing the wt-% amount of the renewable isomeric paraffin composition increases the wt-% amount of renewables in the thermal cracking feedstock and consequently in the cracking product.

In certain embodiments, the sum of the wt-% amounts of the renewable isomeric paraffin composition and of the fossil naphtha is at least 95 wt-%, preferably at least 99 wt-%, of the total weight of the thermal cracking feedstock. Thermal cracking feedstocks comprising mainly the renewable isomeric paraffin composition and fossil naphtha are particularly suitable for thermal cracking.

In certain embodiments, the ratio of the wt-% amount of isoparaffins with more than three branches to the total wt-% amount of the isoparaffins in the renewable isomeric paraffin composition is less than 0.12, preferably less than 0.10, more preferably less than 0.05. Decreasing the ration of the wt-% amount of isoparaffins with more than three branches to the total wt-% amount of the isoparaffins in the renewable isomeric paraffin composition further decreases the total amount of CO, $CO_2$, and $C_2H_2$ formed in the thermal cracking step.

In certain embodiments, of the isoparaffins in the renewable isomeric paraffin composition at least 80 wt-%, preferably at least 85 wt-%, more preferably at least 90 wt-%, even more preferably at least 95 wt-% are in the range of carbon number C14-C18. The total amount of CO, $CO_2$, and $C_2H_2$ formed in the thermal cracking step is further decreased when thermally cracking a thermal cracking feedstocks comprising the renewable isomeric paraffin composition wherein at least 80 wt-% of the isoparaffins in the renewable isomeric paraffin composition are in the range of carbon number C14-C18 compared to thermally cracking a thermal cracking feedstock comprising a renewable paraffin compositions not fulfilling this criterion. The total amount of CO, $CO_2$, $C_2H_2$ formed in the thermal cracking step decreases further as the wt-% of isoparaffins in the range of carbon number C14-C18 in the renewable isomeric paraffin composition increases.

In certain embodiments, of the paraffins in the renewable isomeric paraffin composition 60-95 wt-%, preferably 60-80 wt-%, further preferably 65-70 wt-% are isoparaffins.

Renewable isomeric paraffin compositions comprising at least 60 wt-% isoparaffins have good cold properties and good miscibility with fossil naphtha.

In certain embodiments, the renewable isomeric paraffin composition comprises paraffins at least 70 wt-%, preferably at least 80 wt-%, further preferably at least 90 wt-%, more preferably at least 95 wt-%, and even more preferably at least 99 wt-%, of the total weight of the renewable isomeric paraffin composition. Thermal cracking feedstocks comprising the renewable isomeric paraffin composition having a high paraffin content promote in the thermal cracking step a high yield of C2 and C3 hydrocarbons, such as ethene and propene which are both valuable cracking products.

In certain embodiments, the fossil naphtha comprises 20-85 wt-% paraffins, 0-35 wt-% olefins, 10-30 wt-% naphthenes, and 0-30 wt-% aromatics of the total weight of the fossil naphtha. In certain embodiments, the wt-% of hydrocarbons in the fossil naphtha is at least 95 wt-%, more preferably at least 99 wt-%, of the total weight of the fossil naphtha.

In certain embodiments, the thermal cracking feedstock comprises sulfur 20-300 ppm by weight, preferably 20-250 ppm by weight, more preferably 20-100 ppm by weight, and even more preferably 50-65 ppm by weight. The thermal cracking feedstock comprising sulfur further decreases the formation of CO and $CO_2$ in the thermal cracking step. Because the renewable isomeric paraffin composition comprised in the thermal cracking feedstock already reduces the total amount of CO, $CO_2$, and $C_2H_2$ formed in the thermal cracking step, it is not necessary for the thermal cracking feedstock to contain large amounts of sulfur. A low sulfur amount of the thermal cracking feedstock results in a cracking product with a low sulfur content.

In certain embodiments, step b) is conducted at a coil outlet temperature (COT) selected from the range from 780° C. to 890° C., preferably from 800° C. to 860° C., more preferably from 800° C. to 840° C., and even more preferably from 800° C. to 820° C. A low total amount of CO, $CO_2$, and $C_2H_2$ can be obtained performing the thermal cracking step at a coil outlet temperature (COT) selected from a wide temperature range. Selecting the COT from the range from 800° C. to 840° C. particularly decreases the total amount of CO, CO2, and $C_2H_2$ formed in the thermal cracking step. In certain embodiments, the thermal cracking performed in step b) is steam cracking.

In certain embodiments, the method comprises the step of c) subjecting at least a portion of the cracking product formed in step b) to a purification treatment to remove at least one of CO, $CO_2$, or $C_2H_2$. An advantage of the method according to the first aspect is a reduced burden of removal of CO, $CO_2$, $C_2H_2$, or a combination thereof, which enables efficient purification.

In certain embodiments, the method comprises the step of d) subjecting at least a portion of the cracking product formed in step b), or at least a portion of the cracking product subjected to the purification treatment of step c), or both, to a polymerisation treatment to produce polymers. In certain embodiments, the polymerisation treatment is a catalytic polymerisation treatment. In certain embodiments, the polymerisation treatment comprises contacting at least a portion of the cracking product formed in step b), or at least a portion of the cracking product subjected to the purification treatment of step c), or both, with a polymerisation catalyst, optionally in the presence of molecular hydrogen, to form polymers. The cracking product formed in step b) and optionally purified in step c) is particularly suitable for polymerisation due to the low total amount of polymerisation catalyst poisons CO, $CO_2$, and $C_2H_2$ formed in the thermal cracking step. Further, polymers formed in step d) are at least partially derived from renewable sources and thus more sustainable than polymers derived exclusively from fossil sources.

In certain embodiments, the method comprises providing multiple thermal cracker furnaces, and performing step b) in at least one of the multiple thermal cracker furnaces. In certain embodiments, the method comprises obtaining cracking products from the multiple thermal cracking furnaces, and mixing the obtained cracking products to form a combined cracking product, and optionally subjecting at least a portion of the combined cracking product to a purification treatment to remove at least one of CO, $CO_2$, or $C_2H_2$, or to a polymerisation treatment to form polymers, or to both the purification treatment and the polymerisation treatment.

According to a second aspect of the invention there is provided a thermal cracking feedstock comprising 1-100 wt-% renewable isomeric paraffin composition of the total weight of the thermal cracking feedstock, the renewable isomeric paraffin composition comprising at least 60 wt-% paraffins of the total weight of the renewable isomeric paraffin composition, wherein of said paraffins 10-95 wt-% are isoparaffins, and the ratio of the wt-% amount of isoparaffins with more than three branches to the total wt-% amount of the isoparaffins is less than 0.15, and 0-99 wt-% fossil naphtha of the total weight of the thermal cracking feedstock, the sum of the wt-% amounts of the renewable isomeric paraffin composition and of the fossil naphtha being at least 90 wt-% of the total weight of the thermal cracking feedstock. When subjecting a thermal cracking feedstock comprising a renewable isomeric paraffin composition wherein the ratio of the wt-% amount of isoparaffins with more than three branches to the total wt-% amount of the isoparaffins in the renewable isomeric paraffin composition is less than 0.15 to thermal cracking the total amount of CO, $CO_2$, and $C_2H_2$ formed is less compared to subjecting to thermal cracking a thermal cracking feedstock comprising a renewable paraffinic composition not fulfilling this criterion.

In certain embodiments, the thermal cracking feedstock comprises 50-100 wt-% renewable isomeric paraffin composition of the total weight of the thermal cracking feedstock, and 0-50 wt-% fossil naphtha of the total weight of the thermal cracking feedstock. In certain embodiments, the thermal cracking feedstock comprises 50-85 wt-% renewable isomeric paraffin composition and 15-50 wt-% fossil naphtha, preferably 60-85 wt-% renewable isomeric paraffin composition and 15-40 wt-% fossil naphtha, more preferably 70-85 wt-% renewable isomeric paraffin composition and 15-30 wt-% fossil naphtha of the total weight of the thermal cracking feedstock. Thermal cracking feedstocks comprising at least 50 wt-% of the renewable isomeric paraffin composition promote the formation of high value chemicals (HVCs, i.e. ethene, propene, 1,3-butadiene, benzene, toluene, and xylenes) when subjected to thermal cracking and are more sustainable compared to thermal cracking feedstocks comprising a lower wt-% the renewable isomeric paraffin composition.

In certain embodiments, the sum of the wt-% amounts of the renewable isomeric paraffin composition and of the fossil naphtha is at least 95 wt-%, more preferably at least 99 wt-%, of the total weight of the thermal cracking feedstock.

In certain embodiments, the ratio of the wt-% amount of isoparaffins with more than three branches to the total wt-% amount of the isoparaffins in the renewable isomeric paraffin composition is less than 0.12, preferably less than 0.10, more preferably less than 0.05. Decreasing the ration of the wt-% amount of isoparaffins with more than three branches to the total wt-% amount of the isoparaffins in the renewable isomeric paraffin composition comprised in the thermal cracking feedstock further decreases the total amount of CO, $CO_2$, and $C_2H_2$ formed when the thermal cracking feedstock is subjected to thermal cracking.

In certain embodiments, of the isoparaffins in the renewable isomeric paraffin composition at least 80 wt-%, preferably at least 85 wt-%, more preferably at least 90 wt-%, even more preferably at least 95 wt-%, are in the range of carbon number C14-C18. Thermal cracking feedstocks comprising the renewable isomeric paraffin composition wherein at least 80 wt-% of the isoparaffins in the renewable isomeric paraffin composition are in the range of carbon number C14-C18 further decrease the total amount of CO, $CO_2$, and $C_2H_2$ formed when the thermal cracking feedstock is subjected to thermal cracking compared to subjecting to thermal cracking a thermal cracking feedstock not fulfilling this criterion. This effect becomes more pronounced as the wt-% of isoparaffins in the range of carbon number C14-C18 in the renewable isomeric paraffin composition comprised in the thermal cracking feedstock increases.

In certain embodiments, of the paraffins in the renewable isomeric paraffin composition 60-95 wt-%, preferably 60-80 wt-%, further preferably 65-70 wt-% are isoparaffins. Renewable isomeric paraffin compositions comprising at least 60 wt-% isoparaffins have good cold properties and good miscibility with fossil naphtha.

In certain embodiments, the renewable isomeric paraffin composition comprises paraffins at least 70 wt-%, preferably at least 80 wt-%, further preferably at least 90 wt-%, more preferably at least 95 wt-%, even more preferably at least 99 wt-%, of the total weight of the renewable isomeric paraffin composition. A high paraffin content of the renewable isomeric paraffin composition comprised in the thermal cracking feedstock promotes a high yield of C2 and C3 hydrocarbons, such as ethene and propene, when the thermal cracking feedstock is subjected to thermal cracking In certain embodiments, the fossil naphtha comprises 20-85 wt-% paraffins, 0-35 wt-% olefins, 10-30 wt-% naphthenes, and 0-30 wt-% aromatics of the total weight of the fossil naphtha. In certain embodiments, the wt-% of hydrocarbons in the fossil naphtha is at least 95 wt-%, more preferably at least 99 wt-%, of the total weight of the fossil naphtha.

In certain embodiments, the thermal cracking feedstock comprises sulfur 20-300 ppm by weight, preferably 20-250 ppm by weight, more preferably 20-100 ppm by weight, and most preferably 50-65 ppm by weight. The thermal cracking feedstock comprising sulfur further decreases the formation of CO and $CO_2$ when the thermal cracking feedstock is subjected to thermal cracking. Because the renewable isomeric paraffin composition comprised in the thermal cracking feedstock already reduces the total amount of CO, $CO_2$, and $C_2H_2$ formed when the thermal cracking feedstock is subjected to thermal cracking, it is not necessary for the thermal cracking feedstock to contain large amounts of sulfur.

According to a third aspect of the invention there is provided a cracking product comprising a mixture of hydrocarbons obtainable by a method according to the first aspect, wherein the sum of the wt-% amounts of CO, $CO_2$ and $C_2H_2$ in the cracking product is less than 1.5 wt-%, preferably less than 1.3 wt-%, more preferably less than 1.1 wt-%, even more preferably less than 0.8 wt-% of the total weight of the cracking product.

According to a fourth aspect of the invention there is provided use of the cracking product according to the third aspect for producing polymers, such as polypropene, polyethene, or both. In certain embodiments, the cracking product according to the third aspect is used for producing polymers by a catalytic polymerisation treatment. The cracking product of the third aspect is particularly suitable for polymerisation due to the low total amount of CO, $CO_2$, and $C_2H_2$, which are polymerisation catalyst poisons.

According to a fifth aspect of the invention there is provided an article of manufacture comprising polymers obtainable by a method according to the first aspect comprising step d) or comprising subjecting at least a portion of a combined cracking product to a polymerisation treatment to form polymers. Said polymers comprised in the article of manufacture are at least partially derived from renewable sources and thus the article of manufacture is more sustainable than articles of manufacture comprising polymers derived exclusively from fossil sources.

Different non-binding aspects and embodiments of the present invention have been illustrated in the foregoing. The embodiments in the foregoing are used merely to explain selected aspects or steps that may be utilized in implementations of the present invention. Some embodiments may be presented only with reference to certain aspects of the invention. It should be appreciated that corresponding embodiments may apply to other aspects as well.

BRIEF DESCRIPTION OF THE DRAWINGS

Some example embodiments of the invention will be described with reference to the accompanying drawings, in which:

FIG. 1 shows a schematic drawing of a bench scale steam cracking setup used in the Examples.

DETAILED DESCRIPTION

In the following description, like reference signs denote like elements or steps.

The present invention relates to a method comprising providing a thermal cracking feedstock at least partially derived from renewable sources, namely a thermal cracking feedstock comprising a renewable isomeric paraffin composition, and thermally cracking said thermal cracking feedstock to form a cracking product comprising a mixture of hydrocarbons. Further, the present invention relates to use of the cracking product comprising a mixture of hydrocarbons for producing polymers.

As used herein, a renewable isomeric paraffin composition refers to a composition derived from a renewable source or renewable sources and comprising to a large extent paraffins (non-cyclic alkanes), both linear normal paraffins (n-praffins) and branched isoparaffins (i-paraffins). Said isoparaffins may be monobranched i-paraffins, di-branched i-paraffins, tri-branched i-paraffins, i-paraffins comprising more than three branches, or a combination thereof. Preferably, the isoparaffins are methyl substituted isoparaffins, i.e. isoparaffins wherein the side chain or sidechains, i.e. the branch or branches, are methyl sidechains. In theory, the number of branches may be determined from a structural formula by first identifying the longest carbon chain, and then calculating the branches attached to the longest carbon chain. However, in practice, the number of sidechains (branches) can be determined by any suitable analytical method, such as the analytical method described in the Examples.

It was surprisingly found that thermally cracking renewable paraffinic feedstock tends to increase the production of unwanted by products, particularly the total amount of CO, $CO_2$, and $C_2H_2$, compared to thermally cracking conventional fossil feedstocks, particularly fossil naphtha. This unwanted effect was found to be particularly pronounced when thermally cracking blends of a renewable paraffinic feedstock component and a fossil feedstock component, such as fossil naphtha. CO and $CO_2$ are polymerisation catalyst poisons and therefore, cracking products fed to a polymerisation process should preferably not contain more than 15 ppm by volume, more preferably no more than 0.2 ppm by volume, and even more preferably no more than 0.03 ppm by volume CO and preferably no more than 10 ppm by volume, such as not more than 0.09 ppm by volume, more preferably no more than 0.1 ppm by volume $CO_2$. $C_2H_2$ may also act as a polymerisation catalyst poison, particularly for catalysts in polyethylene production. Thus, cracking products fed to a polymerisation process should preferably contain $C_2H_2$ less than 10 ppm by volume, more preferably less than 2.7 ppm by volume, even more preferably less than 1 ppm by volume. Therefore, there is typically a high burden of removal of CO, $CO_2$, and $C_2H_2$ before cracking products from thermally cracking feedstocks comprising a renewable paraffinic feedstock component can be fed to a polymerisation process.

However, it was surprisingly found that the above described effect of an increased total amount of CO, $CO_2$, and $C_2H_2$ can be mitigated by selecting or providing as a thermal cracking feedstock or as a thermal cracking feedstock component blended with fossil naphtha a renewable isomeric paraffin composition comprising at least 60 wt-% paraffins of the total weight of the renewable isomeric paraffin composition, wherein of said paraffins 10-95 wt-% are isoparaffins, and wherein the ratio of the wt-% amount of isoparaffins with more than three branches to the total wt-% amount of the isoparaffins is less than 0.15, and thermally cracking said thermal cracking feedstock. Thermally cracking a thermal cracking feedstock comprising or consisting of the renewable isomeric paraffin composition wherein the ratio of the wt-% amount of isoparaffins with more than three branches to the total wt-% amount of the isoparaffins is less than 0.15 reduces the total amount of CO, $CO_2$, and $C_2H_2$ formed, compared to thermally cracking feedstocks comprising or consisting of a renewable paraffinic feedstock component not fulfilling said criterion. Surprisingly, without being bound to any theory, the ratio of the wt-% amount of isoparaffins with more than three branches to the total wt-% amount of isoparaffins in the renewable isomeric paraffin composition appears to be an important factor in controlling formation of CO, $CO_2$, and $C_2H_2$ during the thermal cracking process.

In the present disclosure, the weight percentage of paraffins in the renewable isomeric paraffin composition is determined relative to the total weight of the renewable isomeric paraffin composition, and the weight percentages of isoparaffins (total wt-% isoparaffins) and normal paraffins in the renewable isomeric paraffin composition are determined relative to the total weight of paraffins in the renewable isomeric paraffin composition, respectively. Further, in the present disclosure, the weight percentages of monobranched isoparaffins, di- and tribranched isoparaffins, and isoparaffins with more than three branches are determined relative to the total weight of paraffins in the renewable isomeric paraffin composition, respectively. The ratio of the wt-% amount of isoparaffins with more than three branches to the total wt-% amount of the isoparaffins is, in the present disclosure, determined based on the respective weight percentages which are determined relative to the total weight of paraffins in the renewable isomeric paraffin composition.

It was found that by further decreasing the ratio of the wt-% amount of isoparaffins with more than three branches to the total wt-% amount of isoparaffins in the renewable isomeric paraffin composition, the total amount of CO, $CO_2$, and $C_2H_2$ formed in the thermal cracking step is further decreased. Accordingly, in certain embodiments, the ratio of the wt-% amount of isoparaffins with more than three branches to the total wt-% amount of isoparaffins of the renewable isomeric paraffin composition is less than 0.12, preferably less than 0.10, more preferably less than 0.05. The ratio of the wt-% amount of isoparaffins with more than three branches to the total wt-% amount of isoparaffins of the renewable isomeric paraffin composition may be selected from about 0.14, 0.13, 0.12, 0.11, 0.10, 0.09, 0.08, 0.07, 0.06, 0.05, 0.04, 0.03, 0.02, and 0.01. In certain embodiments, the ratio of the wt-% amount of isoparaffins with more than three branches to the total wt-% amount of isoparaffins of the renewable isomeric paraffin composition is at least 0.01. Accordingly, the ratio of the wt-% amount of isoparaffins with more than three branches to the total wt-% amount of isoparaffins of the renewable isomeric paraffin composition may be at least 0.01 and less than 0.15, preferably at least 0.01 and less than 0.12, more preferably at least 0.01 and less than 0.10, and even more preferably at least 0.01 and less than 0.05.

It was further found that by providing as a thermal cracking feedstock a thermal cracking feedstock comprising 1-100 wt-% renewable isomeric paraffin composition of the total weight of the thermal cracking feedstock, the renewable isomeric paraffin composition comprising at least 60 wt-% paraffins of the total weight of the renewable isomeric paraffin composition, wherein of said paraffins 10-95 wt-% is isoparaffins, and wherein of said isoparaffins at least 80 wt-% is in the range of carbon number C14-C18, and wherein the ratio of the wt-% amount of isoparaffins with more than three branches to the total wt-% amount of the isoparaffins is less than 0.15, preferably less than 0.12, more preferably less than 0.10, even more preferably less than 0.05, and 0-99 wt-% fossil naphtha of the total weight of the thermal cracking feedstock, the sum of the wt-% amounts of the renewable isomeric paraffin composition and of the fossil naphtha being at least 90 wt-% of the total weight of the thermal cracking feedstock the total amount of CO, $CO_2$, and $C_2H_2$ formed in the thermal cracking step compared to thermally cracking thermal cracking feedstocks comprising or consisting of a renewable paraffinic feedstock component not fulfilling these criteria. When thermally cracking a thermal cracking feedstock comprising or consisting of the renewable isomeric paraffin composition wherein of the isoparaffins in the renewable isomeric paraffin composition at least 80 wt-% are in the range of carbon number C14-C18 the total amount of CO, $CO_2$, and $C_2H_2$ formed is reduced compared to thermally cracking feedstocks comprising or consisting of a renewable paraffinic feedstock component with isoparaffins having a larger carbon number distribution. It appears, without being bound to any theory, that the carbon number distribution of the isoparaffins in the renewable isomeric paraffin composition is a factor controlling formation of CO, $CO_2$, and $C_2H_2$ during the thermal cracking step. In the present disclosure, the weight percentage of isoparaffins in the range of carbon number C14-C18 is determined relative to the total weight of the isoparaffins in the renewable isomeric paraffin composition.

Increasing the wt-% amount of isoparaffins being in the range of carbon numbers C14-C18 in the renewable isomeric paraffin composition further decreases the total amount of CO, $CO_2$, and $C_2H_2$ formed in the thermal cracking step. Accordingly, in certain embodiments, the isomeric paraffin composition comprises at least 60 wt-% paraffins of the total weight of the renewable isomeric paraffin composition, wherein of said paraffins 10-95 wt-% is isoparaffins, and wherein of said isoparaffins at least 85 wt-%, preferably at least 90 wt %, more preferably at least 95 wt-%, is in the range of carbon number C14-C18, and wherein the ratio of the wt-% amount of isoparaffins with more than three branches to the total wt-% amount of the isoparaffins is less than 0.15. The wt-% amount of isoparaffins of the renewable isomeric paraffin composition in the range of carbon numbers C14-C18 may be selected from about 85 wt-%, 86 wt-%, 87 wt-%, 88 wt-%, 89 wt-%, 90 wt-%, 91 wt-%, 92 wt-%, 93 wt-%, 94 wt-%, 95 wt-%, 96 wt-%, 97 wt-%, 98 wt-%, 99 wt-%, and 100 wt-%.

In certain preferred embodiments, the isomeric paraffin composition comprises at least 60 wt-% paraffins of the total weight of the renewable isomeric paraffin composition, wherein of said paraffins 10-95 wt-% are isoparaffins, and wherein of said isoparaffins at least 90 wt-% are in the range of carbon number C14-C18, and wherein the ratio of the wt-% amount of isoparaffins with more than three branches to the total wt-% amount of the isoparaffins is less than 0.12. More preferably, the isomeric paraffin composition comprises at least 60 wt-% paraffins of the total weight of the renewable isomeric paraffin composition, wherein of said paraffins 10-95 wt-% are isoparaffins, and wherein of said isoparaffins at least 95 wt % are in the range of carbon number C14-C18, and wherein the ratio of the wt-% amount of isoparaffins with more than three branches to the total wt-% amount of the isoparaffins is less than 0.10, preferably less than 0.05. By simultaneously decreasing the ratio of the wt-% amount of isoparaffins with more than three branches to the total wt-% amount of isoparaffins in the renewable isomeric paraffin composition and increasing the wt-% amount of i-paraffins in the range of carbon numbers C14-C18 in the renewable isomeric paraffin composition the total amount of CO, $CO_2$, and $C_2H_2$ formed in the thermal cracking step is particularly low.

Renewable isomeric paraffin compositions comprising at least 60 wt-% isoparaffins have good cold properties and can be stored as such in feed tanks of thermal crackers not equipped with heaters at low ambient temperatures (0° C. or less) without disrupting the cracking process. Good cold properties refers herein to a low temperature value of the cloud point. Increasing the wt-% amount of isoparaffins in the renewable isomeric paraffin composition improves the miscibility of the renewable isomeric paraffin composition with fossil naphtha, which is an advantage when the thermal cracking feedstock comprises less than 100 wt-% of the renewable isomeric paraffin composition and more than 0 wt-% fossil naphtha of the total weight of the thermal cracking feedstock. Accordingly, in certain embodiments, the renewable isomeric paraffin composition comprises at least 60 wt-% paraffins of the total weight of the renewable isomeric paraffin composition, wherein of said paraffins 60-95 wt-%, preferably 65-93 wt-%, more preferably 65-90 wt-% are isoparaffins, and wherein the ratio of the wt-% amount of isoparaffins with more than three branches to the total wt-% amount of the isoparaffins is less than 0.15.

It was found that the undesired effect of an increased total amount of CO, $CO_2$, and $C_2H_2$ described earlier may become more pronounced when the wt-% of isoparaffins in a renewable paraffinic feedstock component is high. Therefore, the beneficial effect of a decreased total amount of CO, $CO_2$, and $C_2H_2$ formed during thermal cracking is particularly important when the renewable isomeric paraffin composition wherein the ratio of the wt-% amount of isoparaffins with more than three branches to the total wt-% amount of the isoparaffins is less than 0.15, and wherein of the isoparaffins in the renewable isomeric paraffin composition preferably at least 80 wt-% is in the range of carbon number C14-C18 comprises at least 60 wt-% isopraffins of the total weight of the paraffins in the renewable isomeric paraffin composition. Accordingly, in certain embodiments, the renewable isomeric paraffin composition comprises at least 60 wt-% paraffins of the total weight of the renewable isomeric paraffin composition, wherein of said paraffins 60-95 wt-%, preferably 65-93 wt-%, more preferably 65-90 wt-% are isoparaffins, and wherein of said isoparaffins at least 85 wt-% are in the range of carbon number C14-C18, and wherein the ratio of the wt-% amount of isoparaffins with more than three branches to the total wt-% amount of the isoparaffins is less than 0.12. Further, in certain embodiments, the renewable isomeric paraffin composition comprises at least 60 wt-% paraffins of the total weight of the renewable isomeric paraffin composition, wherein of said paraffins 60-95 wt-%, preferably 65-93 wt-%, more preferably 65-90 wt-% are isoparaffins, and wherein of said isoparaffins at least 90 wt-% are in the range of carbon number C14-C18, and wherein the ratio of the wt-% amount of isoparaffins with more than three branches to the total wt-% amount of the isoparaffins is less than 0.10, preferably less than 0.05.

In certain embodiments, the renewable isomeric paraffin composition comprises at least 60 wt-% paraffins of the total weight of the renewable isomeric paraffin composition, wherein of said paraffins 60-80 wt-%, preferably 65-70 wt % are isoparaffins, and wherein the ratio of the wt-% amount of isoparaffins with more than three branches to the total wt-% amount of the isoparaffins is less than 0.15, and wherein of the isoparaffins in the renewable isomeric paraffin composition preferably at least 80 wt-% is in the range of carbon number C14-C18. A renewable isomeric paraffin composition having a moderate isomerisation degree, for example a wt-% amount of isoparaffins of 80 wt-% or less, or of 70 wt-% or less, promotes in the thermal cracking step the formation of ethylene, which is a valuable thermal cracking product.

As already mentioned, the total amount of CO, $CO_2$, and $C_2H_2$ formed during thermal cracking can be decreased by decreasing the ratio of the wt-% amount of isoparaffins with more than three branches to the total wt-% amount the isoparaffins in the renewable isomeric paraffin composition. Consequently, low wt-% amounts of isoparaffins with more than three branches in the renewable isomeric paraffin composition are preferred. Preferably, the renewable isomeric paraffin composition comprises isoparaffins with more than three branches less than 14 wt-%, further preferably less than 12 wt-%, yet further preferably less than 10 wt-%, more preferably less than 8 wt-%, even more preferably less than 5 wt-%, and most preferably less than 3 wt-%, such as 1 wt-% or less, or 0.5 wt-% or less, of the total weight of paraffins in the renewable isomeric paraffin composition. The renewable isomeric paraffin composition may comprises isoparaffins with more than three branches 1-14 wt-%, preferably 2-12 wt-%, further preferably 2-10 wt-%, and more preferably 2-5 wt-% of the total weight of paraffins in the renewable isomeric paraffin composition.

Monobranched isoparaffins, particularly monomethyl substituted isoparaffins, promote the formation of propylene, a valuable cracking product, in the thermal cracking step. It is therefore preferred that the renewable isomeric paraffin composition comprises at least 30 wt-%, preferably at least 35 wt-%, further preferably at least 40 wt-%, more preferably at least 45 wt-%, and even more preferably at least 50 wt-% monobranched isoparaffins of the total weight of paraffins in the renewable isomeric paraffin composition. Optionally, in certain embodiments, the ratio of the wt-% amount of monobranched isoparaffins to the total wt-% amount of isoparaffins in the renewable isomeric paraffin composition is at least 0.3, preferably at least 0.4, further preferably at least 0.5, more preferably at least 0.6, even more preferably at least 0.7, and most preferably at least 0.8. As the isoparaffins of the renewable isomeric paraffin composition are either monobranched isoparaffins, di- and tri-branched isoparaffins, isoparaffins with more than three branches, or a combination thereof, the remainder of the isoparaffins is di- and tribranched isoparaffins. In other words, the isoparaffins in the renewable isomeric paraffin composition that are neither monobranched isoparaffins nor isoparaffins with more than three branches are di- and tribranched isoparaffins.

The renewable isomeric paraffin composition has preferably a high paraffin content. A high paraffin content promotes a high yield of C2 and C3 hydrocarbons, such as ethene and propene which are both valuable cracking products, in the thermal cracking step. Therefore, in certain embodiments, the renewable isomeric paraffin composition comprises at least 70 wt-%, preferably at least 80 wt-%, more preferably at least 90 wt-%, even more preferably at least 95 wt-% paraffins of the total weight of the renewable isomeric paraffin composition, wherein of said paraffins 10-95 wt-% are isoparaffins, and wherein the ratio of the wt-% amount of isoparaffins with more than three branches to the total wt-% amount of the isoparaffins is less than 0.15. The wt-% amount of paraffins in the renewable isomeric paraffin composition may be selected from about 65 wt-%, 70 wt-%, 75 wt-%, 80 wt-%, 85 wt-%, 90 wt-%, 95 wt-%, and 99 wt-% of the total weight of the renewable isomeric paraffin composition.

In certain preferred embodiments, the renewable isomeric paraffin composition comprises at least 70 wt-%, preferably at least 80 wt-%, more preferably at least 90 wt-%, even more preferably at least 95 wt-% paraffins of the total weight of the renewable isomeric paraffin composition, wherein of said paraffins 60-95 wt-% are isoparaffins, and wherein of said isoparaffins at least 80 wt-% are in the range of carbon number C14-C18, and wherein the ratio of the wt-% amount of isoparaffins with more than three branches to the total wt-% amount of the isoparaffins is less than 0.15. The total amount of $CO$, $CO_2$, and $C_2H_2$ formed in the thermal cracking step is low, when the thermal cracking feedstock comprises or consists of such renewable isomeric paraffin compositions. Further, such renewable isomeric paraffin compositions have good cold properties and good miscibility in fossil naphtha, and promote the formation of valuable cracking products, such as propene and ethene, in the thermal cracking step.

As mentioned previously, the renewable isomeric paraffin composition has preferably a high wt-% amount of paraffins. Accordingly, the renewable isomeric paraffin composition comprises preferably aromatics (aromatic hydrocarbons) 1.0 wt-% or less, more preferably 0.5 wt-% or less, even more preferably 0.2 wt-% or less, and olefins (alkenes) less than 2.0, preferably 1.0 wt-% or less, more preferably 0.5 wt-% or less, and naphthenes (cycloalkanes) no more than 5.0 wt-%, preferably 2.0 wt-% or less. A low wt-% amount of aromatics, olefins, and naphthenes in the renewable isomeric paraffin composition promotes the formation of high value chemicals (HVCs) in the thermal cracking step. As used herein, high value chemicals refer to ethene, propene, 1,3-butadiene, benzene, toluene, and xylenes. Benzene, toluene, and xylenes may be referred to as BTX. In any case, the renewable isomeric paraffin composition comprises preferably at most 50 ppm by weight oxygen. A low oxygen content allows carrying out the thermal cracking in a more controlled manner, which favours the formation of HVCs. The paraffins in the renewable isomeric paraffin composition are n-paraffins and i-paraffins. The linear n-paraffins tend to crack to ethene molecules. Therefore, it is preferred that the renewable isomeric paraffin composition comprises at least 5 wt-%, such as 5-90 wt-%, n-paraffins of the total weight of the paraffins in the renewable isomeric paraffin composition. In certain embodiments, the renewable isomeric paraffin composition comprises 5-40 wt-%, preferably 8-35 wt-%, further preferably 10-35 wt-%, more preferably 20-35 wt-%, and even more preferably 30-35 wt-% n-paraffins of the total weight of the paraffins in the renewable isomeric paraffin composition.

In general, any renewable isomeric paraffin composition as defined in the foregoing can be used in any aspect or embodiment of the present invention. Nevertheless, certain particularly preferred renewable isomeric paraffin compositions are mentioned in the following. In certain particularly preferred embodiments, the renewable isomeric paraffin composition comprises paraffins at least 80 wt-% of the total weight of the renewable isomeric paraffin composition, wherein of said paraffins 60-93 wt-% are isoparaffins, and wherein of said isoparaffins at least 90 wt-% are in the in the range of carbon numbers C14-C18, and wherein the ratio of the wt-% amount of isoparaffins with more than three branches to the total wt-% amount of the isoparaffins is less than 0.12. Further, in certain particularly preferred embodiments, the renewable isomeric paraffin composition comprises paraffins 90 wt-% of the total weight of the renewable isomeric paraffin composition, wherein of said paraffins 60-90 wt-%, preferably 65-70 wt-%, are isoparaffins, and wherein of said isoparaffins at least 95 wt-% are in the range of carbon numbers C14-C18, and wherein the ratio of the wt-% amount of isoparaffins with more than three branches to the total wt-% amount of the isoparaffins is less than 0.10, preferably less than 0.5. These renewable isomeric paraffin compositions were found to generate a particularly low total amount of $CO$, $CO_2$, and $C_2H_2$ while promoting the formation of HVCs in the thermal cracking step when provided as a thermal cracking feedstock or a thermal cracking feedstock component in a blend with fossil naphtha. Further, these renewable isomeric paraffin compositions have favourable cold properties and blend well with (have good miscibility in) fossil naphtha.

Providing the thermal cracking feedstock may comprise providing the renewable isomeric paraffin composition and providing fossil naphtha, and combining the renewable isomeric paraffin composition with the fossil naphtha to form the thermal cracking feedstock. The renewable isomeric paraffin composition is preferably provided by subjecting a feedstock derived from renewable sources (renewable feedstock), the feedstock comprising fatty acids, fatty acid derivatives, mono-, di- or triglycerides, or a combination thereof, to hydrotreatment to form n-paraffins, and subjecting at least a portion of the n-paraffins formed in the hydrotreatment to an isomerisation treatment to form i-paraffins.

Preferably, the renewable feedstock, i.e. the feedstock derived from renewable sources, comprises at least one of vegetable oil, vegetable fat, animal oil, or animal fat. These materials are preferred, since they allow providing a renewable feedstock having a predictable composition which can be adjusted as needed by appropriate selection and/or blending of the natural oil(s) and/or fat(s). The renewable feedstock may comprise vegetable oil, wood oil, other plant based oil, animal oil, animal fat, fish fat, fish oil, algae oil, microbial oil, or a combination thereof. Optionally, the renewable feedstock may comprise recyclable waste and/or recyclable residue. Recyclable waste comprises material such as used cooking oil, free fatty acids, palm oil by-products or process side streams, sludge, side streams from vegetable oil processing, or a combination thereof. The overall sustainability of the renewable feedstock and consequently also of the renewable isomeric paraffin composition and the formed cracking product may be increased by providing a renewable feedstock comprising recyclable waste, or recyclable residues, or both, either as such or combined with fresh feed of renewable oils and/or renewable fats, such as vegetable oil, vegetable fat, animal oil, and/or animal fat. Fresh feed refers herein to components that have not been recycled. The renewable feedstock may be subjected to optional pre-treatment before subjecting it to hydrotreatment and isomerisation to obtain a renewable isomeric paraffin composition. Such pre-treatment may comprise purification and/or chemical modification of the renewable feedstock, such as saponification or transesterification. If the renewable feedstock is a solid material (at ambient conditions), it is useful to chemically modify the material so as to derive a liquid renewable feedstock, which is preferred.

The hydrotreatment typically serves as a deoxygenation, denitrogenation, and desulfurization treatment of the fatty acids, fatty acid derivatives, and/or the glycerides comprised in the renewable feedstock. Further, providing the renewable isomeric paraffin composition may comprise subjecting the renewable feedstock to decarboxylation and decarbonylation reactions (i.e. removal of oxygen in the form of $CO_x$), and/or other catalytic processes to: remove oxygen from organic oxygen compounds in the form of water, to remove sulfur from organic sulfur compounds in the form of dihydrogen sulfide ($H_2S$), to remove nitrogen from organic nitrogen compounds in the form of ammonia ($NH_3$) and to remove halogens from organic halogen compounds, for example chlorine in the form of hydrochloric acid (HCl). Such processes may be for example hydrodechlorination to remove chlorine and hydrodenitrogenation (HDN) to remove nitrogen.

Preferably, the hydrotreatment is hydrodeoxygenation (HDO), or catalytic hydrodeoxygenation (catalytic HDO). The hydrotreatment is preferably performed at a pressure selected from the range 2-15 MPa, preferably 3-10 MPa, and at a temperature selected from the range 200-500° C., preferably 280-400° C. The hydrotreatment may be performed in the presence of known hydrotreatment catalyst containing metals from Group VIII and/or VIB of the Periodic System. Preferably, the hydrotreatment catalysts are supported Pd, Pt, Ni, NiW, NiMo or a CoMo catalyst, wherein the support is alumina and/or silica. Typically, $NiMo/Al_2O_3$ and/or $CoMo/Al_2O_3$ catalysts are used.

The renewable isomeric paraffin composition of the present invention may be provided by subjecting at least a portion of the n-paraffins formed in the hydrotreatment step to an isomerisation treatment to form i-paraffins and to produce the renewable isomeric paraffin composition. The isomerisation treatment is not particularly limited. Nevertheless, catalytic isomerisation treatments are preferred. Typically, subjecting n-paraffins formed in the hydrotreatment step from the renewable feedstock to an isomerisation treatment forms predominantly methyl substituted isoparaffins. The severity of isomerization conditions and choice of catalyst controls the amount of methyl branches formed and their distance from each other in the carbon backbone. The isomerization step may comprise further intermediate steps such as a purification step and a fractionation step. Purification and/or fractionation steps allows better control of the properties of the renewable isomeric paraffin composition being formed.

The isomerization treatment is preferably performed at a temperature selected from the range 200-500° C., preferably 280-400° C., and at a pressure selected from the range 2-15 MPa, preferably 3-10 MPa. The isomerization treatment may be performed in the presence of known isomerization catalysts, for example, catalysts containing a molecular sieve and/or a metal selected from Group VIII of the Periodic Table and a carrier. Preferably, the isomerization catalyst is a catalyst containing SAPO-11 or SAPO-41 or ZSM-22 or ZSM-23 or ferrierite and Pt, Pd, or Ni and $Al_2O_3$ or $SiO_2$. Typical isomerisation catalysts are, for example, $Pt/SAPO-11/Al_2O_3$, $Pt/ZSM-22/Al_2O_3$, $Pt/ZSM-23/Al_2O_3$ and/or $Pt/SAPO-11/SiO_2$. Catalyst deactivation may be reduced by the presence of molecular hydrogen in the isomerisation treatment. Therefore, the presence of added hydrogen in the isomerisation treatment is preferred. In certain embodiments, the hydrotreatment catalyst(s) and the isomerization catalyst(s) are not in contact with the reaction feed (the renewable feedstock and/or n-paraffins and/or i-paraffins derived therefrom) at the same time. In certain embodiments, the hydrotreatment and the isomerisation treatment are conducted in separate reactors, or carried out separately.

In certain embodiments, only a portion of the n-paraffins formed in the hydrotreatment step is subjected to an isomerization treatment. A portion of the n-paraffins formed in the hydrotreatment step may be separated, the separated n-paraffins then subjected to the isomerisation treatment to form i-paraffins. After being subjected to the isomerisation treatment, the separated paraffins are optionally re-unified with the remainder of the paraffins. Alternatively, all of the n-paraffins formed in the hydrotreatment step may be subjected to the isomerization treatment to form i-paraffins.

Incidentally, the isomerisation treatment is a step which predominantly serves to isomerise the paraffins of the renewable isomeric paraffin composition. While most thermal or catalytic conversions (such as hydrotreatment and HDO) result in a minor degree of isomerisation (usually less than 5 wt-%), the isomerisation step which may be employed in the present invention is the step which leads to a significant increase in the isoparaffin content of the renewable isomeric paraffin composition. Typically, the carbon number distribution does not substantially change during the isomerisation treatment. Accordingly, the wt-% amount of paraffins in the range of carbon numbers C3-C14 does not substantially increase in the course of the isomerisation treatment. This is favourable, as isoparaffins with carbon number less than C14 have been found to increase the formation of CO, $CO_2$, and $C_2H_2$ in the thermal cracking step.

Providing the renewable isomeric paraffin composition does preferably not comprise gasifying renewable feedstock. Paraffin compositions manufactured through gas-to-liquid (GTL) processes, such as processes comprising a Fischer-Tropsch process step, are characterized by broad distribution of paraffinic hydrocarbons in the range of carbon numbers C9-C50, particularly C9-C24.

Water and light gases, such as carbon monoxide, carbon dioxide, hydrogen, methane, ethane, and propane, may be separated from the hydrotreated and/or isomerised renewable feedstock with any conventional means, such as distillation, before providing the renewable isomeric paraffin composition as a thermal cracking feedstock or thermal cracking feedstock component. After or along with removal of water and light gases, the hydrotreated and/or isomerised renewable feedstock may be fractionated to one or more fractions. The fractionation may be conducted by any conventional means, such as distillation. Further, the hydrotreated and/or isomerised renewable feedstock may optionally be purified. The purification and/or fractionation allows better control of the properties of the isomeric paraffin composition being formed, and thus the properties of the cracking product of the thermal cracking step. However, a renewable isomeric paraffin composition obtained by hydrotreatment and isomerisation of renewable feedstock as described above may be fed directly to a thermal cracker or thermal cracking process.

The isoparaffin content and the types of isoparaffins (braching of the isoparaffins) in the renewable isomeric paraffin composition are mainly controlled by the isomerisation treatment; e.g. the catalyst (or lack thereof), the temperature, the pressure, the residence time, and the amount of added hydrogen in the isomerisation process. In certain embodiments, providing the renewable isomeric paraffin composition comprises analysing the renewable isomeric paraffin composition obtained from the isomerisation treatment, and, based on the analysis results, selecting a renewable isomeric paraffin composition fulfilling the previously described requirements, and providing the selected renewable isomeric paraffin composition as a thermal cracking feedstock or as a thermal cracking feedstock component. By selecting a renewable isomeric paraffin composition fulfilling the previously described criteria, the total amount of unwanted by-products, namely CO, $CO_2$, and $C_2H_2$, formed during thermal cracking can be reduced. Preferably, analysing the renewable isomeric paraffin composition comprises determining the wt-% paraffins in the renewable isomeric paraffin composition, determining the wt-% isoparaffins in the renewable isomeric paraffin composition, determining the ratio of the wt-% amount of isoparaffins with more than three branches to the total wt-% amount of the isoparaffins in the renewable isomeric paraffin composition, and preferably determining the carbon number distribution of the isoparaffins in the renewable isomeric paraffin composition. Analysing the renewable isomeric paraffin composition may further comprise determining the wt-% n-paraffins in the renewable isomeric paraffin composition, and/or determining the weight percentages of monobranched isoparaffins, di- and tribranched isoparaffins, and isoparaffins with more than three branches, respectively. The weight percentages of paraffins, isoparaffins, n-paraffins, as well as of monobranched isoparaffins, di- and tribranched isoparaffins, and isoparaffins with more than three branches may be determined with any suitable method, for example using GC-FID analysis, such as the analytical method described in the Examples.

The thermal cracking feedstock of the present invention comprises, based on the total weight of the thermal cracking feedstock, 1-100 wt-% of the renewable isomeric paraffin composition described in the foregoing, and 0-99 wt-% of fossil naphtha, the sum of the wt-% amounts of the renewable isomeric paraffin composition and of the fossil naphtha being at least 90 wt-% of the total weight of the thermal cracking feedstock. In other words, the renewable isomeric paraffin composition may be provided as the thermal cracking feedstock, or as a thermal cracking feedstock component combined with fossil naphtha to form the thermal cracking feedstock. Preferably, the sum of the wt-% amount renewable isomeric paraffin composition and the wt-% amount fossil naphtha is at least 95 wt-%, and more preferably at least 99 wt-% of the total weight of the thermal cracking feedstock.

As used herein, fossil naphtha refers to a composition which is naturally occurring and derived from non-renewable sources. Such non-renewable sources may also be referred to as "fossil sources" or "mineral sources". Examples of non-renewable sources, from which the fossil naphtha may be derived, include crude oil, petroleum oil/gas, shale oil/gas, natural gas, or coal deposits, and the like, and combinations thereof, including any hydrocarbon-rich deposits that can be utilized from ground/underground sources. Such sources may also be referred to as "fossil oil". Fossil naphtha comprises mainly hydrocarbons. In certain embodiments, the fossil naphtha comprises hydrocarbons at least 95 wt-%, preferably at least 99 wt-%, of the total weight of the fossil naphtha. In certain embodiments, the fossil naphtha comprises 20-85 wt-% paraffins, 0-30 wt-%, preferably 0-5 wt-%, olefins (alkenes), 5-30 wt-% naphthenes (cycloalkanes), and 0-30 wt-% aromatics (aromatic hydrocarbons) of the total weight of the fossil naphtha.

The fossil naphtha may be selected from various grades of fossil naphtha, such as heavy naphtha, light naphtha, or combinations thereof. Preferably, the boiling point range (initial boiling point to end point) of the fossil naphtha is within the temperature range from 25° C. to 360° C. In certain embodiment, the boiling point range of the fossil naphtha is within the range from 25° C. to 220° C. Further, in certain embodiments, the boiling point range of the fossil naphtha is within the range from 30° C. to 90° C., preferably from 35° C. to 85° C. Yet further, in certain embodiments, the boiling point range of the fossil naphtha is within the range from 50° C. to 200° C., preferably from 50° C. to 187° C. In yet certain embodiments, the boiling point range of the fossil naphtha is within the range from 180° C. to 360° C. The boiling point ranges are given as measured according to EN-ISO-3405 (2011).

In certain embodiments, the thermal cracking feedstock comprises, based on the total weight of the renewable isomeric paraffin composition, 50-100 wt-% of the renewable isomeric paraffin composition, and 0-50 wt-% fossil naphtha. In certain preferred embodiments, the thermal cracking feedstock comprises, based on the total weight of the thermal cracking feedstock, 50-85 wt-% of the renewable isomeric paraffin composition and 15-50 wt-% fossil naphtha, preferably 60-85 wt-% of the renewable isomeric paraffin composition and 15-40 wt-% fossil naphtha, more preferably 70-85 wt-% of the renewable isomeric paraffin composition and 15-30 wt-% fossil naphtha. A thermal cracking feedstock comprising at least 50 wt-% of the renewable isomeric paraffin composition, or comprising mainly the renewable isomeric paraffin composition, is preferred. The renewable isomeric paraffin composition promotes formation of HVCs in the thermal cracking step compared to fossil naphtha and increases the sustainability of the thermal cracking feedstock, and consequently the sustainability of the formed cracking product. In certain embodiments, the thermal cracking feedstock comprises the renewable isomeric paraffin composition and fossil naphtha in a weight ratio of 5:1 (renewable isomeric paraffin composition to fossil naphtha).

The thermal cracking of the present invention is preferably steam cracking. Steam cracking facilities are widely used in petrochemical industry and particularly as a raw material source for polymer industry. The processing conditions of steam cracking are well known, the implementation of the present invention thus requiring only few modifications of established processes. Thermally cracking the above described thermal cracking feedstock is preferably performed in a conventional naphtha (steam) cracker, i.e. a cracker commonly used for thermally cracking fossil naphtha. The thermal cracking is preferably carried out without catalyst. However, additives, particularly sulfur additives, may be used in the thermal cracking step. The method of the present invention may comprise providing a thermal cracking feedstock comprising sulfur to reduce coke formation, and to further reduce the formation of CO and $CO_2$ in the thermal cracking step. The formation of $C_2H_2$ in the thermal cracking step is not significantly influenced by the sulfur content of the thermal cracking feedstock. Without being bound to any theory, it is believed that sulfur passivates active sites on the cracking coil surface, particularly Ni sites of the cracking coil material, by forming nickel sulfides. Nickel sulfides do not catalyse coke gasification, in contrast to metallic Ni and Ni oxides.

To further reduce the formation of CO and $CO_2$ in the thermal cracking step, the thermal cracking feedstock may comprise sulfur. Renewable isomeric paraffin compositions provided by hydrotreatment and isomerisation of renewable feedstock, particularly of vegetable oils/fats and/or animal oils/fats, are chemically mixtures of mainly paraffinic hydrocarbons comprising a very low quantity of sulfur. Without sulfur additisation, the renewable isomeric paraffin composition may comprise sulfur less than 5 ppm by weigh. Sulfur may be added to the thermal cracking feedstock by adding a sulfur containing compound (sulfur additive) to the thermal cracking feedstock, or by providing a thermal cracking feedstock comprising the renewable isomeric paraffin composition and a sufficient amount of fossil naphtha typically comprising sulfur, or both. Accordingly, in certain embodiments, the thermal cracking feedstock comprises sulfur 20-300 ppm by weight, preferably 20-250 ppm by weight, more preferably 20-100 ppm by weight, even more preferably 20-65 ppm by weight. Because the renewable isomeric paraffin composition of the present invention already reduces the total amount of unwanted by-products (CO, $CO_2$, and $C_2H_2$) formed during thermal cracking, it is not necessary for the thermal cracking feedstock to contain large amounts of sulfur. A low sulfur concentration of the thermal cracking feedstock has the advantage that the cracking product, particularly its heavier hydrocarbon fractions, also has a low sulfur content. Typically, the heavier hydrocarbon fractions of the cracking product (C4 and above) are not subjected to extensive purification after they have been separated from the cracking product, and therefore sulfur originating from the thermal cracking step substantially remains in these fractions. The pyrolysis gasoline (PyGas) fraction, comprising typically mainly C4-C11 hydrocarbons, particularly C5-C9 hydrocarbons from which benzene has been removed, is typically diverted to a so called fuel pool, i.e. used as a fuel component. Low or ultra-low sulfur fuels and fuel components are preferred, because fuels with a low sulfur content or fuels free from sulfur produces less harmful emissions upon combustion than fuels or fuel components with a higher sulfur content. A thermal cracking feedstock comprising sulfur 50-65 ppm by weight is particularly preferred, because a sulfur content of 50-65 ppm by weight further reduces the formation of CO and $CO_2$ in the thermal cracking step and forms a PyGas fraction with a low sulfur content (without post-fractionation purification steps).

Examples of suitable sulfur additives are dimethyl disulfide (DMDS), hydrogen sulfide ($H_2S$), and carbon disulfide ($CS_2$). DMDS is a particularly preferred sulfur additive, because DMDS reduces coking. In certain embodiments, providing the thermal cracking feedstock comprises mixing sulfur additive, preferably DMDS, with the thermal cracking feedstock to form a thermal cracking feedstock comprising sulfur 20-300 ppm by weight, preferably 20-250 ppm by weight, more preferably 20-100 ppm by weight, even more preferably 20-65 ppm by weight. In certain preferred embodiments, providing the thermal cracking feedstock comprises mixing sulfur additive, preferably DMDS, with the thermal cracking feedstock to form a thermal cracking feedstock comprising sulfur 50-65 ppm by weight. Sulfur additive may be mixed with the thermal cracking feedstock before feeding the thermal cracking feedstock to the thermal cracking step. Optionally, sulfur additive may be added in the thermal cracking step by injecting into a thermal cracking furnace steam comprising sulfur additive. Accordingly, in certain embodiments, the method comprises injecting into a thermal cracking furnace steam comprising sulfur additive, preferably DMDS, such that the thermal cracking feedstock in the thermal cracking furnace comprises sulfur 20-300 ppm by weight, preferably 20-250 ppm by weight, more preferably 20-100 ppm by weight, even more preferably 20-65 ppm by weight. In certain preferred embodiments, the method comprises injecting into a thermal cracking furnace steam comprising sulfur additive, preferably DMDS, such that the thermal cracking feedstock in the furnace comprises sulfur 50-65 ppm by weight.

In certain embodiments, providing the thermal cracking feedstock comprises combining fossil naphtha with the renewable isomeric paraffin composition to form a thermal cracking feedstock comprising sulfur 20-300 ppm by weight, preferably 20-250 ppm by weight, more preferably 20-100 ppm by weight, even more preferably 20-65 ppm by weight. In certain preferred embodiments, providing the thermal cracking feedstock comprises combining fossil naphtha with the renewable isomeric paraffin composition to form a thermal cracking feedstock comprising sulfur 50-65 ppm by weight. The sulfur concentration of fossil naphtha may vary depending on the source of the fossil naphtha and the refining steps it has been subjected to. Providing a thermal cracking feedstock comprising a predetermined amount of sulfur may comprise selecting fossil naphtha with a suitable sulfur content, adjusting the wt-% of fossil naphtha in the thermal cracking feedstock, or both. A thermal cracking feedstock comprising a predetermined amount of sulfur may thus be provided without addition of sulfur additive. Nevertheless, sulfur additive may optionally be added to a thermal cracking feedstock comprising fossil naphtha and the renewable isomeric paraffin composition.

By providing as thermal cracking feedstock the thermal cracking feedstock of the present invention a favourable, low amount of impurities (CO, $CO_2$, $C_2H_2$) can be obtained performing the thermal cracking step at a coil outlet temperature (COT) selected from a wide temperature range. The COT is usually the highest temperature for the thermal cracking feedstock in the thermal cracker. The thermal cracking step is preferably performed at a COT selected from the range from 780 to 890° C., preferably from the range from 800 to 860° C. The total amount of unwanted by-products (CO, $CO_2$, and $C_2H_2$) formed in the thermal cracking step is particularly low when the COT is selected from the range from 800° C. to 840° C. The COT may, for example, be selected from about 805° C., 810° C., 815° C., 820° C., 825° C., 830° C., and 835° C. A particularly low total amount of unwanted by-products (CO, $CO_2$, and $C_2H_2$) is formed when the thermal cracking is conducted at a COT of about 800° C. Thermal cracking feedstocks comprising both the renewable isomeric paraffin composition and fossil naphtha form particularly low amounts of CO, $CO_2$, and $C_2H_2$ when the COT is selected from the range from 800° C. to 820° C.

In certain embodiments, in which the thermal cracking is steam cracking, the steam cracking is performed at a flow rate ratio between water and the thermal cracking feedstock ($H_2O$ flow rate [kg/h]/thermal cracking feedstock flow rate [kg/h]) of 0.05-1.20, preferably 0.10-1.00, further preferably 0.20-0.80, more preferably 0.25-0.70, even more preferably 0.25-0.60, and most preferably 0.30-0.50. In certain preferred embodiments, in which the thermal cracking is steam cracking, the steam cracking is performed at a flow rate ratio between water and the thermal cracking feedstock ($H_2O$ flow rate [kg/h]/thermal cracking feedstock flow rate [kg/h]) of 0.30-0.50 and at a COT selected from the range from 800° C. to 840° C. Performing the steam cracking at these conditions result in a low total amount of CO, $CO_2$, and $C_2H_2$.

The coil outlet pressure in the thermal cracking step may be selected from the range 0.09-0.3 MPa, preferably at least 0.1 MPa, more preferable at least 0.11 MPa or 0.12 MPa, and preferably at most 0.25 MPa, more preferably at most 0.22 MPa or 0.20 MPa.

The thermal cracking process may comprise recycling unconverted reactants back to the thermal cracking furnace. Optionally, certain less valuable portions of the cracking product, such as propane and ethane, may be recycled back to the thermal cracking furnace to be converted to more valuable products, such as ethene and propene. Recycling unconverted reactants, less valuable portions of the cracking product, or both, increases the overall profitability and the overall yield of the thermal cracking process and/or the overall yield of HVCs.

The thermal cracking may be performed in multiple thermal cracking furnaces. The thermal cracking feedstock of the present invention comprising or consisting of the renewable isomeric paraffin composition may be fed to one or more of the multiple thermal cracker furnaces. For example, availability of the renewable isomeric paraffin composition may determine how many of the multiple thermal cracker furnaces may be fed with the thermal cracking feedstock of the present invention. The effluents, or cracking products, of the multiple steam crackers may be combined to form one or more effluent streams optionally transported or conveyed to further processing steps, such as purification and/or polymerisation. Optionally, the thermal cracking may be performed in a single thermal cracker furnace fed with the thermal cracking feedstock of the present invention, and the effluent, or cracking product, from the single thermal cracking furnace may optionally be transported or conveyed to further processing steps, such as purification and/or polymerisation.

The steam cracking process may comprise quenching and cooling the cracking product. Typically, at least a portion of CO, $CO_2$, $C_2H_2$, or a combination thereof, is removed from the cracking product during the quenching and cooling. In certain embodiments, the method comprises fractionating the cracking product comprising a mixture of hydrocarbons. The fractionation may comprise separating from the cracking product a fuel oil fraction, a PyGas fraction, a hydrogen fraction, a methane fraction, a fuel gas fraction, a C2 fraction (ethylene fraction), C3 fraction (propylene fraction), and/or a C4 fraction. The C2 fraction (ethylene fraction) and the C3 fraction (propylene fraction) are particularly suitable to be used for producing polymers. Thus, in certain embodiments, the method comprises separating from the cracking product an ethylene fraction, a propylene fraction, or both, and subjecting the ethylene fraction, the propylene fraction, or both to a polymerisation treatment.

The present invention allows obtaining a cracking product having a low total amount of CO, $CO_2$, and $C_2H_2$ by thermally cracking the thermal cracking feedstock of the present invention. In certain embodiments, the cracking product include one or more of hydrogen, methane, ethane, ethene, propane, propene, propadiene, butane, butylenes, such as butene, iso-butene, and butadiene, C5+ hydrocarbons, such as aromatics, benzene, toluene, xylenes, C5-C18 paraffins, or C5-C18 olefins. Optionally, at least a portion of the hydrocarbons included in the cracking product may be further processed into a derivative or derivatives, such as a methane derivative or methane derivatives, an ethene derivative or ethene derivatives, a propene derivative or propene derivatives, a benzene derivative or benzene derivatives, a toluene derivative or toluene derivatives, and/or a xylene derivative or xylene derivatives.

Methane derivatives include, for example, ammonia, methanol, phosgene, hydrogen, oxochemicals and their derivatives, such as methanol derivatives. Examples of methanol derivatives are methyl methacrylate, polymethyl methacrylate, formaldehyde, phenolic resins, polyurethanes, methyl-tert-butyl ether, and their derivatives.

Ethene derivatives include, for example, ethylene oxide, ethylene dichloride, acetaldehyde, ethylbenzene, alpha-olefins, and polyethylene, and their derivatives, such as ethylene oxide derivatives, ethylbenzene derivatives, and acetaldehyde derivatives. Ethylene oxide derivatives include, for example, ethylene glycols, ethylene glycol ethers, ethylene glycol ethers acetates, polyesters, ethanol amines, ethyl carbonates and their derivatives. Ethylbenzene derivatives include, for example, styrene, acrylonitrile butadiene styrene, styrene-acrylonitrile resin, polystyrene, unsaturated polyesters, and styrene-butadiene rubber, and their derivatives. Acetaldehyde derivatives include, for example, acetic acid, vinyl acetate monomer, polyvinyl acetate polymers, and their derivatives. Ethyl alcohol derivatives include, for example, ethyl amines, ethyl acetate, ethyl acrylate, acrylate elastomers, synthetic rubber, and their derivatives. Further, ethene derivatives include polymers, such as polyvinyl chloride, polyvinyl alcohol, polyester such as polyethylene terephthalate, polyvinyl chloride, polystyrene, and their derivatives.

Propene derivatives include, for example, isopropanol, acrylonitrile, polypropylene, propylene oxide, acrylic acid, allyl chloride, oxoalcohols, cumens, acetone, acrolein, hydroquinone, isopropylphenols, 4-hethylpentene-1, alkylates, butyraldehyde, ethylene-propylene elastomers, and their derivatives. Propylene oxide derivatives include, for example, propylene carbonates, allyl alcohols, isopropanolamines, propylene glycols, glycol ethers, polyether polyols, polyoxypropyleneamines, 1,4-butanediol, and their derivatives. Allyl chloride derivatives include, for example, epichlorohydrin and epoxy resins. Isopropanol derivatives include, for example, acetone, isopropyl acetate, isophorone, methyl methacrylate, polymethyl methacrylate, and their derivatives. Butyraldehyde derivatives include, for example, acrylic acid, acrylic acid esters, isobutanol, isobutylacetate, n-butanol, n-butylacetate, ethylhexanol, and their derivatives. Acrylic acid derivatives include, for example, acrylate esters, polyacrylates and water absorbing polymers, such as super absorbents, and their derivatives.

Butylene derivatives include, for example, alkylates, methyl tert-butyl ether, ethyl tert-butyl ether, polyethylene copolymer, polybutenes, valeraldehyde, 1,2-butylene oxide, propylene, octenes, sec-butyl alcohol, butylene rubber, methyl methacrylate, isobutylenes, polyisobutylenes, substituted phenols, such as p-tert-butylphenol, di-tert-butyl-p-cresol and 2,6-di-tert-butylphenol, polyols, and their derivatives. Other butadiene derivatives may be styrene butylene rubber, polybutadiene, nitrile, polychloroprene, adiponitrile, acrylonitrile butadiene styrene, styrene-butadiene copolymer latexes, styrene block copolymers, styrene-butadiene rubber.

Benzene derivatives include, for example, ethyl benzene, styrene, cumene, phenol, cyclohexane, nitrobenzene, alkylbenzene, maleic anhydride, chlorobenzene, benzene sulphonic acid, biphenyl, hydroquinone, resorcinol, polystyrene, styrene-acrylonitrile resin, styrene-butadiene rubber, acrylonitrile-butadiene-styrene resin, styrene block copolymers, bisphenol A, polycarbonate, methyl diphenyl diisocyanate and their derivatives. Cyclohexane derivatives include, for example, adipic acid, caprolactam and their derivatives. Nitrobenzene derivatives include, for example, aniline, methylene diphenyl diisocyanate, polyisocyanates and polyurethanes. Alkylbenzene derivatives include, for example, linear alkybenzene. Chlorobenzene derivatives include, for example, polysulfone, polyphenylene sulfide, and nitrobenzene. Phenol derivatives include, for example, bisphenol A, phenol form aldehyde resins, cyclohexanone-cyclohexenol mixture (KA-oil), caprolactam, polyamides, alkylphenols, such as p-nonoylphenol and p-dedocylphenol, ortho-xylenol, aryl phosphates, o-cresol, and cyclohexanol.

Toluene derivatives include, for example, benzene, xylenes, toluene diisocyanate, benzoic acid, and their derivatives.

Xylene derivatives include, for example, aromatic diacids and anhydrates, such as terephthalic acid, isophthalic acid, and phthalic anhydride, and phthalic acid, and their derivatives. Derivatives of terephthalic acid include, for example, terephthalic acid esters, such as dimethyl terephthalate, and polyesters, such as polyethylene terephthalate, polytrimethylene terephthalate, polybutylene terephthalate and polyester polyols. Phthalic acid derivatives include, for example, unsaturated polyesters, and PVC plasticizers. Isophthalic acid derivatives include, for example, unsaturated polyesters, polyethylene terephthalate co-polymers, and polyester polyols.

The hydrocarbons of the cracking product obtained with the method of the present invention are particularly suitable as raw materials for conventional petrochemistry, and in particular polymer industry. Specifically, the mixture of hydrocarbons comprised in the cracking product obtained with the method of the present invention show a product distribution which is similar to, and even favourable over (comprising a higher wt-% of HVCs), the product distribution of the hydrocarbons obtained from thermal cracking (steam cracking) of conventional fossil raw material, such as fossil naphtha. It is thus possible to produce for example polymers derived partially from renewable material by providing as a thermal cracking feedstock the thermal cracking feedstock of the present invention. Optionally, polymers derived exclusively from renewable material may be produced by providing as the thermal cracking feedstock a thermal cracking feedstock of the present invention consisting of the renewable isomeric paraffin composition.

In certain embodiments, the method comprises subjecting at least a portion of the cracking product to a purification treatment to remove at least one of CO, $CO_2$, or $C_2H_2$. An advantage of the method of the present invention is a low total amount of CO, $CO_2$, and $C_2H_2$ in the cracking product formed in the thermal cracking step and consequently a reduced burden of removal of CO, $CO_2$, $C_2H_2$, or a combination thereof, from the cracking product. This is particularly advantageous in embodiments were at least a portion of the cracking product is subjected to a polymerisation treatment. As mentioned previously, CO, $CO_2$, and $C_2H_2$ are polymerisation catalyst poisons and thus undesirable in a polymerisation process. The burden of removal of CO, $CO_2$, $C_2H_2$, or a combination thereof, from a portion of the cracking product to be subjected to a polymerisation treatment may be greatly reduced, potentially even redundant. In practice, however, a portion of the cracking product to be subjected to a polymerisation treatment is usually first subjected to a purification treatment, for example, as a precaution or to avoid deviations from standard procedures. In any case, a lower amount of CO, $CO_2$, and/or $C_2H_2$ impurities in the cracking product increases the life time of active material, such as an absorbent, an adsorbent, a reactant, a molecular sieve and/or a purification catalyst, which may be used in the purification treatment to remove at least one of CO, $CO_2$, or $C_2H_2$, and decreases the regeneration frequency of the active material.

The purification treatment to which at least a portion of the cracking product may be subjected can be any purification treatment suitable for removing at least one of CO, $CO_2$, or $C_2H_2$. Examples of such purification treatments are described in EP2679656A1, WO2016023973, WO2003048087, and US2010331502A1, all of which are incorporated herein by reference in their entirety.

In certain embodiments, the purification treatment comprises contacting at least a portion of the cracking product with an active material, such as an absorbent, an adsorbent, a purification catalyst, a reactant, a molecular sieve, or a combination thereof, to remove at least one of CO, $CO_2$, or $C_2H_2$. Optionally, the purification treatment may comprise contacting at least a portion of the cracking product with the active material in presence of molecular oxygen, molecular hydrogen, or both. In certain embodiments, the purification treatment comprises passing at least a portion of the cracking product through at least one purification train comprising active material, or at least one bed of active material. The contacting may be performed in a single vessel. Optionally, the contacting may be performed in multiple vessels preferably connected in series, i.e. allowing the portion of the cracking product to be purified to be passed from one vessel to the next for further purification.

The active material may comprise, for example, copper oxide or a copper oxide catalyst, oxides of Pt, Pd, Ag, V, Cr, Mn, Fe, Co, or Ni optionally supported on alumina, $Au/CeO_2$ optionally supported on alumina, zeolites, in particular type A and/or type X zeolites, alumina based absorbents or catalysts, such as a Selexsorb™ COS or Selexord™ CD, a molecular sieve comprising alumina, aluminosilicates, aluminophosphates or mixtures thereof, or any combination thereof.

The active material may comprise an adsorbent or adsorbents as described in WO03/048087A1 on p. 11, ll 12-p. 12, ll. 3; p. 12, ll. 18-p. 15, ll. 29, and/or p. 17, ll. 21-p. 21, ll. 2 and/or a molecular sieve or molecular sieves as described in WO03/048087A1 on p. 21, ll. 3-p. 22 ll. 26. The active material may comprise a purification catalyst or catalysts as described in US2010/0331502A1, paragraphs to [0116], or a molecular sieve or molecular sieves as described in US2010/0331502A1, paragraphs [0117] to [0119]. The active material may comprise a purification catalyst or catalysts as described in WO2016/023973A1, paragraph [0061], [0062], [0063], and/or [0064].

The purification treatment may be a purification treatment as described in EP2679656A1, paragraphs [0043] to [0082]. The purification treatment may be a purification treatment as described in US2010/0331502A1, paragraphs [0092] to [0119], and/or paragraph [0126], and/or Example 2. The purification treatment may be a purification treatment as described in WO2016/023973A1, paragraphs [0056] to [0067]. The purification treatment may be a purification treatment as described in WO03/048087A1, p. 11, ll. 12-p. 15, ll. 29, and/or p. 16, ll. 1-p. 21, ll. 2, and/or p. 23, ll. 14-p. 24, ll. 13, and/or Example 1 and/or Example 2.

Typically, impurities deactivate or foul the active material during purification treatment. Thus, the active material may be regenerated to at least partially regain its purification activity. Any regeneration process suitable for re-activating the active material may be used. For example, the active material may be regenerated as described in WO2016/023973A1, paragraphs p. 12, ll. 3-10, or as described in EP2679656A1, paragraphs [0108] to [0118], or as described in WO03/048087A1, p. 24, ll. 14-p. 25 ll. 32. For example, a CuO catalyst may be regenerated by contacting the CuO catalyst with $H_2$. A $CuO_2$ catalyst may be regenerated by contacting the $CuO_2$ catalyst with molecular oxygen. A zeolitic molecular sieve may be regenerated by applying heat and contacting the zeolitic molecular sieve with an inert gas flow, such as a nitrogen flow.

In certain embodiments, the purification treatment comprises at least one of the following steps: i) contacting at least a portion of the cracking product with a CuO catalyst to remove oxygen, ii) contacting at least a portion of the cracking product with $H_2$ to remove $C_2H_2$ by hydrogenation, iii) contacting at least a portion of the cracking product with a $CuO_2$ catalyst to remove CO by oxidation, or iv) contacting at least a portion of the cracking product with a zeolitic molecular sieve to remove $CO_2$. Optionally, the purification treatment may comprises removing secondary impurities, such as at least one of COS, $H_2S$, or $CS_2$, by contacting at least a portion of the cracking product with an activated alumina catalyst, such as Selexorb™.

In certain embodiments, the method comprises subjecting at least a portion of the cracking product to a polymerisation treatment to form polymers. The portion of the cracking product subjected to the polymerisation treatment may be obtained directly from the thermal cracking process or from the purification treatment described in the previous sections. Optionally, the portion of the cracking product subjected to the polymerisation treatment may partially have been subjected to the purification treatment described in the previous sections and partially be obtained directly from the thermal cracking process. As mentioned previously, due to the low amount of CO, $CO_2$, and $C_2H_2$ in the cracking product formed in the thermal cracking step, subjecting the cracking product or a portion thereof to a purification treatment before polymerisation may be redundant. In certain preferred embodiments, the portion of the cracking product subjected to the polymerisation treatment is an ethylene fraction, a propylene fraction, or a combination thereof. Consequently, in certain embodiments, the method comprises subjecting an ethylene fraction of the cracking product to a polymerisation treatment to form polyethylene, and optionally subjecting a propylene fraction of the cracking product to a polymerisation treatment to form polypropylene.

The polymerisation treatment may include solution polymerisation, gas-phase fluidized bed polymerisation, slurry phase polymerisation, such as bulk polymerisation, high-pressure polymerisation, or a combination thereof. The polymerisation treatment may be performed in one or more polymerisation reactors. Each of the one or more polymerisation reactors may comprise multiple polymerisation zones. The composition of the feed fed to the polymerisation zones may vary between the zones. For example, different portions of the cracking product may be fed to different zones and a comonomer may optionally be fed to one or more of the polymerisation zones. The comonomer fed to the polymerisation zones may be a different comonomer for different polymerisation zones. The polymerisation reactor may, for example, be a continuous stirred tank type reactor, a fluidised bed type reactor, such as a gas-phase fluidised bed reactor, or a stirred gas-phase type reactor in horizontal or vertical configuration.

Preferably, the polymerisation treatment is catalytic polymerisation. In certain embodiments, the polymerisation treatment comprises contacting at least a portion of the cracking product with a polymerisation catalyst optionally in the presence of molecular hydrogen to form polymers. Preferably, the contacting is performed in one or more polymerisation reactors.

In embodiments, wherein the polymerisation treatment is a catalytic polymerisation treatment, the molecular weight of the formed polymers may be regulated, for example, by the presence of hydrogen in the polymerisation treatment or by controlling the reaction temperature, depending on the polymerisation catalyst(s) employed. In embodiments, wherein the polymerisation treatment is a catalytic polymerisation treatment, the polydispersity is mainly controlled by the catalyst employed.

The polymerisation treatment may be a polymerisation treatment forming polymers having monomodal, bimodal, or multimodal molecular weight distributions. Bimodality or multimodality may be achieved by employing a bi-functional catalyst system in one reaction media (i.e. one reactor or polymerisation zone), or with a typical catalyst (i.e non-bi-functional) but with variable reaction media (i.e. combination of multiple polymerisation zones or multiple polymerisation reactors with different feeds). Other properties of the polymers formed in the polymerisation treatment, such as polarity, unsaturation content and/or polydispersity, may be controlled by controlling the reaction temperature, pressure and residence time, or through injecting a predetermined type and amount of co- and/or termonomers to the polymerisation process at a predetermined location, e.g. in one or more of the polymerisation zones optionally comprised in the polymerisation reactor(s).

Optionally, the density, elastic modulus and other properties of the polymers formed in the polymerisation treatment may be controlled by introducing to the polymerisation treatment a comonomer or combinations of multiple monomers, for example at least one of ethylene (in polypropylene production), propylene (in polyethylene production), 1-butene, 1-hexene (also (1,5-hexadiene), 1-octane (also 1,7-octadiene) and 1-decene (also 1,9-octadiene) or higher alpha olefins or alpha-omega dienes.

In certain embodiments, the polymerisation treatment is a slurry polymerisation treatment comprising dissolving in a diluent, such as propane, propene or hexane, at least a portion of the cracking product together with molecular hydrogen, and optionally a comonomer, to form a solution, and contacting the solution with a catalyst to form polymers.

In certain embodiment, the polymerisation treatment is high pressure polymerisation preferably carried out in an autoclave reactor or a tubular reactor. Typically, high pressure polymerisation does not utilise catalysts. Both the autoclave reactor and the tubular reactor may comprise multiple polymerisation zones to which at least a portion of the cracking product may be fed optionally together with a comonomer. The composition of the feed fed to the polymerisation zones may vary between the zones as mentioned previously. The high pressure polymerisation may be initiated with various initiators such as molecular oxygen, t-amyl organic peroxide, or t-butyl peroxyesters, or blends thereof. The molecular weight of the polymers formed in the high pressure polymerisation may optionally be controlled by using chain transfer agents, such as methyl ethyl ketone (MEK), propionaldehyde, alpha olefins, di-olefins, or a combination thereof. In certain preferred embodiments, the portion of the cracking product subjected to the high pressure polymerisation is the ethylene fraction. Examples of polymers which may be formed in the high pressure polymerisation of the ethylene fraction are low density polyethylene (LDPE), or LDPE copolymers or LDPE terpolymers with vinyl acetate and/or other esters, such as methyl, ethyl, or butyl acrylates, glycidyl methacrylate, and/or acid groups, such as acrylic acid or methacrylic acid, and/or silanes, such as vinyltrimethoxysilane, and/or acid anhydrides, such as maleic anhydride.

The polymerisation treatment may be a polymerisation treatment as described in EP2679656A1, paragraphs [0090]-[0097]. The polymerisation treatment may be a polymerisation treatment as described in US2010/0331502A1, paragraphs [0050]-[0066], and/or paragraphs [0123]-[0125], and/or Example 3. The polymerisation treatment may be a polymerisation treatment as described in WO2016/023973, paragraphs [0006]-[0020], and/or paragraphs [0024]-[0043]. The method may comprise a combination of a purification treatment and a polymerisation treatment as described in US2010/0331502A1, paragraphs [0092]-[0119].

Preferably, the portion of the cracking product subjected to the polymerisation treatment is an ethylene fraction of the cracking product and polyethylene (PE), or co- or terpolymers thereof, is thus formed in the polymerisation treatment. Ethylene monomers of the cracking product may be homopolymerized or copolymerized with one or more comonomers, such as 1-propylene, 1-butene, 1-pentene, 1-hexene, 1-octene, and/or conjugated and non-conjugated diolefins, such as butadiene, 1,3-pentadiene, 2,3-dimethylbutadiene, 1,4-pentadiene, 1,5-hexadiene and/or vinylcyclohexene. Preferably, ethylene is copolymerized with 1-butene, 1-octene, or 1-hexene. Examples of polymerisation treatments to form PE, or co- or terpolymers thereof, comprise monomodal processes, and/or multimodal processes, including hybrid processes. Linear polyethylene of various density ranges from ultra-low density polyethylene (ULDPE), very low density polyethylene (VLDPE), linear low density polyethylene (LLDPE), medium density polyethylene (MDPE) through to high density polyethylene (HDPE) homo/copolymers, random and block co/terpolymers through multimodality may be formed in the polymerisation treatment of the ethylene fraction by, for example, slurry polymerisation, bulk polymerisation (i.e. a slurry process diluent and monomer are the same), solution phase polymerisation, gas phase polymerisation, and/or multi reactor combinations of either the same or hybrid technologies operated in parallel or in series (so called cascade) producing either similar (i.e. mono-modal) or dissimilar (i.e. bi-modal, tri-modal, or multi-modal) polymers in various ratios, or splits between each reactor.

The portion of the cracking product subjected to the polymerisation treatment may preferably be the propylene fraction of the cracking product and polypropylene (PP), or co- or terpolymers thereof, is thus formed in the polymerisation treatment. Polypropylenes of different density ranges and product classes, such as homopolymers, high crystallinity homo-polymers, random co-polymers, impact co-polymers, block co/terpolymers, hetero-phasic co-polymers, or combinations thereof may be formed in the polymerisation treatment of the propylene fraction.

An example of a polymerisation catalyst for catalytic polymerisation, particularly of the ethylene fraction and/or the propylene fraction, is Ziegler type catalysts, which utilise aluminum alkyl compounds, such as trimethylaluminum, triethylaluminum, tri-isobutylaluminum, methylaluminoxane (MAO), or tri-n-hexylaluminum as co-catalyst activators to activate titanium or vanadium sites on the catalyst, such as titanium tetrachloride. The aluminium alkyl compounds can additionally be used as scavengers of polymerisation poisons in the reaction media.

The polymerisation catalyst for catalytic polymerisation may be supported if desired or required by the process. The support material may be magnesium dichloride or silica support onto which active sites and optionally internal donors, such as benzoate, phthalate, diether, or succinate may be impregnated. Additionally, external donors, such as ethyl p-ethoxybenzoate (PEEB), dicyclopentyldimethoxysilane (DCPMS), diisopropyldimethoxysilane (DIPS), diisobutyldimethoxysilane, cyclohexyldimethoxymethylsilane (CHMMS), dicyclopentyldimethoxysilane (DPDMS), or alkoxysilanes, such as Me(EtO)3Si, Ph(EtO)3Si,Ph2(MeO)2Si, Ph2(EtO)2Si, Ph2(EtO)2Si, Ph(EtO)3Si, may be added to the polymerisation treatment.

In certain embodiments, the polymerisation catalyst is a stereo modifiers, such as cyclohexylmethyldimethoxysilane, dicyclopentyldimethoxysilane, diisobutyldimethoxysilane, diisopropyldimethoxysilane, isobutylisopropyldimethoxysilane, n-propyltrimethoxysilane, isobutylmethyldimethoxysilane, tetraethoxysilane, tetramethoxysilane, isobutyltriethoxysilane, n-propyltriethoxysilane, isobutyltrimethoxysilane, and/or cyclohexylethyldimethoxysilane.

A further example of a polymerisation catalyst for catalytic polymerisation, particularly of the ethylene fraction and/or the propylene fraction, are so called single site catalyst systems of which there are various types, such as Kaminsky type, combination type, constrained-geometry type, and late transition metal catalyst type.

The polymerisation catalyst may contain a metallocene complex of zirconium, titanium, or hafnium which usually contains two cyclopentadienyl rings or monolobal equivalents to cyclopentadienyl and either a perfluorinated boron-aromatic compound, an organoaluminum compound, or methylaluminoxane where the rings contain various alkyl substituents, both linear and cyclic. Said rings may be linked together by bridging groups. Alternatively, the polymerisation catalyst may contain monocyclopentadienyl derivatives of titanium or zirconium, one of the carbon atoms in the cyclopentadienyl ring being additionally linked to the metal atom by a bridge.

These complexes which may be contained in the polymerisation catalyst are typically converted to polymerization catalysts by reacting said complexes with methylaluminoxane or by forming ionic complexes with noncoordinative anions. Other complexes, such as cyclopentadienyl group 4 ketimide complexes, cyclopentadienyl group 4 siloxyl complexes, and/or non-cyclopentadienyl group 4 phosphinimide complexes may optionally be used for forming polymerisation catalysts.

A further type of polymerisation catalysts for catalytic polymerisation is Phillips type catalysts which may comprise hexavalent chromium supported on a high-surface-area, wide-pore oxide carrier, such as silica, alumina, titania, aluminophosphates, or combinations where a mixture of chromium oxide and silicon oxide ($CrO_3/SiO_2$) may be used to create active sites.

The polymerisation catalyst may be a polymerisation catalyst as described in EP2679656A1, paragraphs [0098]-[0107]. The polymerisation catalyst may be a polymerisation catalyst as described in US2010/0331502A1, paragraphs [0067]-[0091], and/or Example 1. The polymerisation catalyst may be a polymerisation catalyst as described in WO2016/023973A1, paragraphs [0045]-[0055].

The properties of the polymers formed in a catalytic polymerisation treatment, such as molecular weight, molecular weight distribution, long chain branching content, density, viscosity, crystallinity, amorphous content, shear thinning behaviour, other rheological parameters, composition distribution indicators such as comonomer distribution breadth index (CDBI), comonomer distribution constant (CDC), thermal stability, melting temperature, crystallisation temperature, melt flow rate (MFR) and others, may be influenced by selection of the catalyst type or catalysts types (as hybrid versions are available and it is possible to feed two or more different catalysts to one or more reactors), the comonomer type, comonomer content, additional monomer (s) and their type and amount(s).

After the polymerisation process, the formed polymers may be further modified to form polymer martial. The formed polymers may be modified via one or more extrusion or compounding steps where additional ingredients are optionally added. Such additional ingredients are, for example, stabilisation additives, impact modifiers such as plastomers or elastomers, other blend components in general, fillers such as talc's, glass fibres, carbon fibres, nanoclays or other nanomaterials, carbon black, nucleating agents (which are also possible to add in-situ during the polymerisation treatment or preparation of a polymerisation catalyst), UV stabilisers, pigments, crosslinking or visbreaking agents such as organic peroxides, acid scavengers such as calcium stearate, polymer processing aids for example fluropolymers. Additional comonomers or functional groups, such as silanes and/or maleic anhydride, may optionally be added to the formed polymers after the polymerisation treatment via reactive extrusion. The formed polymers may after the polymerisation treatment be subjected to further processing steps in conversion such as thermally initiated crosslinking of organic peroxides (for example a PEX-A process), introduction of catalysts to promote condensation reactions, such as silane crosslinking reactions (for example a PEX-B process) or crosslinking reactions induced by radiation (e.g., a PEX-C process). These optional modifications enable production of at least partially bio-based (renewable) versions of the full spectrum of fossil based polymer materials, particularly PE and/or PP materials, and other materials and articles derived from these polymer materials.

The polymers formed in the polymerisation treatment, or the polymer material derived from the formed polymers as described above, may be converted or formed to final parts or products by multiple processes such as extrusion processes for film, sheet, fibres, pipe, profiles, wires and cables, injection moulding processes, hot melt spinning, blow moulding or extrusion blow moulding processes, rotational moulding processes, hot dip coating, calendaring, compacting, chemical and/or physical foaming processes or others. The polymer material derived from the polymers formed in the polymerisation treatment may be used as a direct substitute for fossil based polymer materials in these conversion processes. The polymer material derived from the polymers formed in the polymerisation treatment may optionally be blended with other types of polymers, fillers, additives, or combinations thereof and may optionally be included in composite materials or multilayer structures with other materials, such as other polymer materials, for example fossil based polypropylene, polyvinylidene chloride, polyesters, ethylene vinyl alcohol, aluminium, etc.

The final parts or products described above may be used in a variety of applications. For example, said final parts or products may be used in packaging applications including food and non-food packaging, flexible packaging, heat seal, thin wall packaging, transparent packaging, packaging of dangerous goods, packaging for detergents and personal care, packaging of surfactants, etc. Said final parts or products may be used in consumer goods applications such as caps and closures, toys, bottles, watering cans, white goods and appliances, engineering parts, crates, cartridges, leisure products, housewares, panels and profiles, lids, shoe insoles, pipe clamps, car boot/trunk lining, brushes, corks, ink cartridges, flippers, brushes, collector trays for perforators, seals, hand grips, garden furniture, houseware, thin walled injection moulded parts, co-injection moulded parts, food containers, reusable containers, luggage, ice cream containers, dairy products containers, drinking cups, high impact containers, high stiffness containers, DVD boxes, etc. Said final parts or products may be used in automotive applications, such as parts and assemblies for exterior, interior, under-the-bonnet, bumpers, body panels, trims, facias, dashboards, door claddings, climate control or cooling systems, air intake manifolds or battery cases, instrument panels or soft touch controls, airbag covers, roof pillar mouldings, under the hood belt or hoses, weather strips, anti-vibration systems, rocker panels or side moulding, instrument panels, structural parts, etc. Said final parts or products may be used in wire and cable applications, such as insulation, jacketing or semi-conductive materials for extra-high, high and medium voltage energy transmission and distribution in AC or DC, data or communication cables or jacketing, building wires or cables, automotive wires or cables, photovoltaic encapsulants, etc. Said final parts or products may be used in pipe applications such as multilayer pipes, pressure pipes, gas pipes, drinking water pipes, industrial pipes, waste water or sewage pipes, in-house plumbing or heating, mono or multi-layer onshore or offshore oil or gas pipeline coatings, pressure pipes for sandless bedding, no dig installation pipes, linings and relinings, corrugated industrial pipes, fittings, mechanical-joint compression fittings, solar heat absorbers, etc. Said final parts or products may be used in film applications, such as heavy duty bags, liners, refuse sacks, carrier bags, agricultural films, building or construction films, heavy duty shrink films, collation shrink films, fine shrink films, food packaging fill form seal (FFS) films or bags, packaging films for sanitary articles, freezer films, sanitary films, embossed release films, lamination films, label films, cling films, surface protection films, sealing layers, cereal packaging, silicon coated films, stretch hoods, etc. Said final parts or products may be used in fibre applications, such as non-woven or technical fibres, continuous filament, filament yarn, raffia, tapes, strapping nets, bulk fibres, etc. Other applications wherein said final parts or products may be used in are, for example, extrusion coating, hot melt adhesives, tie-layer adhesives, medical applications, roofing & waterproofing membranes, carpeting, rubberized surfaces, artificial turf, base resin for masterbatches and compounding.

Carbon atoms of renewable origin comprise a higher number of $^{14}C$ isotopes compared to carbon atoms of fossil origin. Therefore, it is possible to distinguish between a carbon compound derived from renewable (bio-based) raw material and carbon compounds derived from fossil (fossil based) raw material by analysing the ratio of $^{12}C$ and $^{14}C$ isotopes. Thus, a particular ratio of said isotopes can be used as a "tag" to identify a renewable carbon compound and differentiate it from non-renewable carbon compounds. The isotope ratio does not change in the course of chemical reactions. Therefore, the isotope ratio can be used for identifying renewable isomeric paraffin compositions, renewable hydrocarbons, renewable monomers, renewable polymers, and materials and products derived from said polymers, and distinguishing them from non-renewable feeds and products.

EXAMPLES

The following examples are provided to better illustrate the claimed invention and are not to be interpreted as limiting the scope of the invention. To the extent that specific materials are mentioned, it is merely for purposes of illustration and is not intended to limit the invention.

Steam cracking experiments illustrating certain embodiments of the present invention where carried out on a bench scale equipment. The main parts of the steam cracking unit, the analytical equipment and the calibration procedure used in these examples have been described in detail in the following publications K. M. Van Geem, S. P. Pyl, M. F. Reyniers, J. Vercammen, J. Beens, G. B. Marin, On-line analysis of complex hydrocarbon mixtures using comprehensive two-dimensional gas chromatography, Journal of Chromatography A. 1217 (2010) 6623-6633 and J. B. Beens, U. A. T. Comprehensive two-dimensional gas chromatography—a powerful and versatile technique. Analyst. 130 (2005) 123-127. Two different renewable isomeric paraffin compositions P1 and P2, as well as blends of said renewable isomeric paraffin compositions and fossil naphtha N1 were studied as steam cracking feedstocks. Further, as comparative examples, fossil naphtha N1, a third renewable isomeric paraffins composition P3, and a blend of the third renewable isomeric paraffin composition and fossil naphtha N1 were studied as steam cracking feedstocks.

The bench scale equipment is described with reference to FIG. 1. The feed section controls the supply of the steam cracking feedstock and the water from reservoirs 1 and 2, respectively, to the reactor coil 3. The flow of liquids was regulated by coriolis flow meter controlled pumps 4 (Bronkhorst, The Netherlands) equipped with Bronkhorst™ CORI-FLOW™ series mass flow metering instruments to provide high accuracy: ±0.2% of reading. CORI-FLOW™ mass flow metering instruments utilizes an advanced Coriolis type mass flow sensor to achieve reliable performance, even with changing operating conditions, e.g. pressure, temperature, density, conductivity and viscosity. The pumping frequency was automatically adjusted by the controller of the CORI-FLOW™ flow metering instrument. The mass flow rate, which contrary to the volume flow rate is not affected by changes in temperature or pressure, of all feeds was measured every second, i.e. substantially continuously. Steam was used as a diluent and was heated to the same temperature as the evaporated feedstock. Both the feedstock and the steam were heated in electrically heated ovens 5 and 6, respectively. Downstream from ovens 5 and 6, the feedstock and the steam were mixed in an electrically heated oven 7 filled with quartz beads, which enabled an efficient and uniform mixing of feedstock and the diluent prior to entering the reactor coil 3. The mixture of feedstock and diluent steam entered the reactor coil 3 placed vertically in a rectangular electrically heated furnace 8. Eight thermocouples T positioned along the axial reactor coordinate measured the process gas temperature at different positions. The rectangular furnace 8 was divided into eight separate sections which could be controlled independently to set a specific temperature profile. The pressure in the reactor coil 3 was controlled by a back pressure regulator (not shown) positioned downstream from the outlet of the reactor coil 3. Two pressure transducers (not shown), placed at the inlet and outlet of the reactor, indicated the coil inlet (CIP) and the coil outlet pressure (COP), respectively. At the reactor outlet, nitrogen was injected to the reactor effluent as an internal standard for analytical measurements and to a certain extent contribute to the quenching of the reactor effluent. The reactor effluent was sampled online, i.e. during operation of the steam cracking setup, at a high temperature (350° C.). Namely, via a valve-based sampling system and uniformly heated transfer lines a gaseous sample of the reactor effluent was injected into a comprehensive two-dimensional gas chromatograph (GC×GC) 9 coupled to a Flame Ionization detector (FID) and a Mass Spectrometer (MS). A high temperature 6-port 2-way sampling valve of the valve-based sampling system was placed in an oven, where the temperature was kept above the dew point of the effluent sample. Further downstream the reactor effluent was cooled to approximately 80° C. Water and condensed heavier products (pyrolysis gasoline (PyGas) and pyrolysis fuel oil (PFO)) were removed by means of a knock-out vessel and a cyclone 10, while the remainder of the effluent stream was sent directly to a vent. Before reaching the vent, a fraction of the effluent was withdrawn for analysis on a Refinery Gas Analyzer (RGA) 11. After removal of all remaining water using a water-cooled heat exchanger and dehydrator, this effluent fraction was injected automatically onto the so-called Refinery Gas Analyzer (RGA) 11 using a built-in gas sampling valve system (80° C.).

The compositions of the renewable isomeric paraffin compositions, namely P1, P2, and P3, were analysed by gas chromatography (GC). Samples of the renewable isomeric paraffin composition were analysed as such, without any pretreatment. The method is suitable for hydrocarbons C2-C36. N-paraffins and groups of isoparaffins (C1-, C2-, C3-substituted and ≥C3-substituted) were identified using mass spectrometry and a mixture of known n-paraffins in the range of C2-C36. The chromatograms were split into three groups of paraffins (C1-, C2-/C3- and ≥C3-substituted isoparaffins/n-paraffin) by integrating the groups into the chromatogram baseline right after n-paraffin peak. N-paraffins were separated from ≥C3-substituted isoparaffins by integrating the n-alkane peak tangentially from valley to valley and compounds or compound groups were quantified by normalisation using relative response factor of 1.0 to all hydrocarbons. The limit of quantitation for individual compounds was 0.01 wt-%. Settings of the GC are shown in Table 1.

TABLE 1

Settings of GC determination of n- and i-paraffins.

GC

| | |
|---|---|
| Injection | split/splitless-injector |
| | Split 80:1 (injection volume 0.2 μL) |
| Column | DB™-5 (length 30 m, i.d. 0.25 m, phase thickness 0.25 μm) |
| Carrrie gas | He |
| Detector | FID (flame ionization detector) |
| GC program | 30° C. (2 min)-5° C./min-300° C. (30 min), constant flow 1.1 mL/min |

The analysis results are summarized in Table 2 and detailed results are shown in Tables 3, 4, and 5, respectively. For paraffins in the range of carbon numbers C2-C10 the wt-% amount of n-paraffins and the total wt-% amount of i-paraffins (total i-paraffins), based on the total weight of paraffins in the renewable isomeric paraffin composition, were determined. For paraffins with carbon number C11 or above, the wt-% amounts, based in the total weight of paraffins in the renewable isomeric paraffin composition, of n-paraffins, monobranched i-paraffins, di- and tribranched i-paraffins, and i-paraffins with more than three branches were determined.

The cloud point of each renewable isomeric paraffin composition P1, P2, and P3 was measured according to ASTMD7689-17. The result are shown in Table 2.

TABLE 2

Summary of renewable isomeric paraffin compositions P1, P2, and P3.

| | Cloud Point (° C.) | Total iP wt-% | iP(>tri) wt-% | iP(>tri)/ Total iP | wt-% iP in carbon number range C14-C18 |
|---|---|---|---|---|---|
| P3 (comparative) | −48 | 94.81 | 15.77 | 0.17 | 79.37 |
| P2 | −36 | 92.52 | 10.48 | 0.11 | 92.28 |
| P1 | −2 | 69.04 | 2.88 | 0.04 | 95.46 |

P1 comprised, based on the total weight of paraffins in P1, approximately 31 wt-% n-paraffins and approximately 69 wt-% i-paraffins. The total amount of paraffins in P1 was approximately 99 wt-% of the total weight of P1. Said paraffins were in the range of carbon numbers C6-C24, and of said paraffins approximately 95 wt-% was in the range of carbon numbers C14-C18. Of the i-paraffins, also approximately 95 wt-% was in the range of carbon numbers C14-C18. P1 comprised, based on the total weight of the paraffins, approximately 53 wt-% monomethyl substituted isoparaffins, approximately 12 wt-% di- and triethyl substituted isoparaffins, and approximately 3 wt-% isoparaffins with more than three methyl branches.

TABLE 3

Composition of renewable isomeric paraffin composition P1.

| | P1 | | | | |
|---|---|---|---|---|---|
| Carbon Number | nP | iP(total) | iP(mono) | iP(di and tri) | iP(>tri) |
| 2 | 0.00 | 0.00 | | | |
| 3 | 0.00 | 0.00 | | | |
| 4 | 0.00 | 0.00 | | | |
| 5 | 0.00 | 0.00 | | | |
| 6 | 0.06 | 0.03 | | | |
| 7 | 0.14 | 0.21 | | | |
| 8 | 0.14 | 0.23 | | | |
| 9 | 0.16 | 0.27 | | | |
| 10 | 0.15 | 0.30 | | | |
| 11 | 0.15 | 0.29 | 0.19 | 0.10 | 0.00 |
| 12 | 0.19 | 0.31 | 0.20 | 0.09 | 0.01 |
| 13 | 0.25 | 0.39 | 0.28 | 0.10 | 0.02 |
| 14 | 0.43 | 0.65 | 0.49 | 0.14 | 0.02 |
| 15 | 5.57 | 8.20 | 6.59 | 1.41 | 0.21 |
| 16 | 9.58 | 18.85 | 15.06 | 3.18 | 0.61 |
| 17 | 5.26 | 13.27 | 10.30 | 2.43 | 0.54 |
| 18 | 8.73 | 24.94 | 19.03 | 4.52 | 1.39 |
| 19 | 0.06 | 0.30 | 0.20 | 0.07 | 0.03 |
| 20 | 0.06 | 0.31 | 0.22 | 0.06 | 0.03 |
| 21 | 0.01 | 0.04 | 0.03 | 0.01 | 0.01 |
| 22 | 0.01 | 0.05 | 0.04 | 0.01 | 0.01 |
| 23 | 0.01 | 0.04 | 0.03 | 0.01 | 0.00 |
| 24 | 0.01 | 0.06 | 0.04 | 0.01 | 0.01 |
| 25 | 0.00 | 0.00 | 0.00 | 0.00 | 0.00 |
| C25-C29 | 0.00 | 0.16 | | | |
| C30-C36 | 0.00 | 0.12 | | | |
| >C36 | 0.00 | 0.00 | | | |
| Total | 30.96 | 69.04 | 52.69 | 12.14 | 2.88 |

P2 comprised, based on the total weight of the paraffins in P2, approximately 7 wt-% n-paraffins and approximately 93 wt-% i-paraffins. The total amount of paraffins in P2 was approximately 100 wt-% of the total weight of P2. Said paraffins were in the range of carbon numbers C4-C36, and of said paraffins approximately 92 wt-% was in the range of carbon numbers C14-C18. Of the i-paraffins, also approximately 92 wt-% was in the range of carbon numbers C14-C18. P2 comprised, based on the total weight of the paraffins, approximately 38 wt-% monomethyl substituted isoparaffins, approximately 42 wt-% di- and triethyl substituted isoparaffins, and approximately 10 wt-% isoparaffins with more than three methyl branches.

TABLE 4

Composition of renewable isomeric paraffin composition P2.

| | P2 | | | | |
|---|---|---|---|---|---|
| Carbon Number | nP | iP(total) | iP(mono) | iP(di and tri) | iP(>tri) |
| 2 | 0.00 | 0.00 | | | |
| 3 | 0.00 | 0.00 | | | |
| 4 | 0.01 | 0.00 | | | |
| 5 | 0.02 | 0.01 | | | |
| 6 | 0.05 | 0.04 | | | |
| 7 | 0.09 | 0.12 | | | |
| 8 | 0.26 | 0.51 | | | |
| 9 | 0.23 | 0.76 | | | |
| 10 | 0.19 | 0.91 | | | |
| 11 | 0.15 | 0.93 | 0.66 | 0.27 | 0.00 |
| 12 | 0.13 | 1.08 | 0.67 | 0.38 | 0.03 |

TABLE 4-continued

Composition of renewable isomeric paraffin composition P2.

| Carbon Number | P2 | | | | |
|---|---|---|---|---|---|
| | nP | iP(total) | iP(mono) | iP(di and tri) | iP(>tri) |
| 13 | 0.11 | 1.12 | 0.64 | 0.43 | 0.05 |
| 14 | 0.35 | 1.73 | 0.92 | 0.72 | 0.09 |
| 15 | 1.53 | 9.88 | 5.13 | 4.07 | 0.67 |
| 16 | 1.60 | 26.60 | 11.64 | 12.24 | 2.73 |
| 17 | 1.88 | 15.40 | 7.54 | 6.31 | 1.56 |
| 18 | 0.79 | 31.77 | 10.14 | 16.65 | 4.98 |
| 19 | 0.04 | 0.47 | 0.15 | 0.20 | 0.12 |
| 20 | 0.02 | 0.39 | 0.12 | 0.14 | 0.14 |
| 21 | 0.01 | 0.11 | 0.05 | 0.03 | 0.03 |
| 22 | 0.01 | 0.12 | 0.05 | 0.04 | 0.04 |
| 23 | 0.01 | 0.09 | 0.04 | 0.03 | 0.02 |
| 24 | 0.01 | 0.09 | 0.03 | 0.03 | 0.03 |
| 25 | 0.00 | 0.01 | 0.00 | 0.00 | 0.01 |
| C25-C29 | 0.00 | 0.32 | | | |
| C30-C36 | 0.00 | 0.07 | | | |
| >C36 | 0.00 | 0.00 | | | |
| Total | 7.48 | 92.52 | 37.78 | 41.52 | 10.48 |

Comparative P3 comprised, based on the total weight of paraffins in P3, approximately 5 wt-% n-paraffins and approximately 95 wt-% i-paraffins. The total amount of paraffins in P3 was approximately 97 wt-% of the total weight of P3. Said paraffins were in the range of carbon numbers C4-C36, and of said paraffins approximately 78 wt-% was in the range of carbon numbers C14-C18. Of the i-paraffins, approximately 79 wt-% was in the range of carbon numbers C14-C18. P3 comprised, based on the total weight of the paraffins, approximately 29 wt-% monomethyl substituted isoparaffins, approximately 41 wt-% di- and triethyl substituted isoparaffins, and approximately 16 wt-% isoparaffins with more than three methyl branches.

TABLE 5

Composition of renewable isomeric paraffin composition P3 (comparative examples).

| Carbon Number | P3 | | | | |
|---|---|---|---|---|---|
| | nP | iP(total) | iP(mono) | iP(di and tri) | iP(>tri) |
| 2 | 0.00 | 0.00 | | | |
| 3 | 0.00 | 0.00 | | | |
| 4 | 0.01 | 0.01 | | | |
| 5 | 0.03 | 0.03 | | | |
| 6 | 0.06 | 0.10 | | | |
| 7 | 0.18 | 0.39 | | | |
| 8 | 0.49 | 1.81 | | | |
| 9 | 0.44 | 2.82 | | | |
| 10 | 0.36 | 3.29 | | | |
| 11 | 0.28 | 2.02 | 0.35 | 1.66 | 0.00 |
| 12 | 0.22 | 4.43 | 1.36 | 1.72 | 1.36 |
| 13 | 0.17 | 3.24 | 1.21 | 1.75 | 0.28 |
| 14 | 0.42 | 4.00 | 1.53 | 2.04 | 0.43 |
| 15 | 1.07 | 12.18 | 5.92 | 4.80 | 1.46 |
| 16 | 0.27 | 16.82 | 5.96 | 8.86 | 2.00 |
| 17 | 0.83 | 20.86 | 8.44 | 8.86 | 3.56 |
| 18 | 0.31 | 21.39 | 4.21 | 10.91 | 6.27 |
| 19 | 0.01 | 0.62 | 0.20 | 0.26 | 0.16 |
| 20 | 0.01 | 0.44 | 0.09 | 0.17 | 0.18 |
| 21 | 0.00 | 0.09 | 0.04 | 0.03 | 0.02 |
| 22 | 0.00 | 0.07 | 0.02 | 0.02 | 0.03 |

TABLE 5-continued

Composition of renewable isomeric paraffin composition P3 (comparative examples).

| Carbon Number | P3 | | | | |
|---|---|---|---|---|---|
| | nP | iP(total) | iP(mono) | iP(di and tri) | iP(>tri) |
| 23 | 0.00 | 0.03 | 0.01 | 0.01 | 0.01 |
| 24 | 0.00 | 0.02 | 0.01 | 0.01 | 0.01 |
| 25 | 0.00 | 0.00 | 0.00 | 0.00 | 0.00 |
| C25-C29 | 0.00 | 0.12 | | | |
| C30-C36 | 0.00 | 0.03 | | | |
| >C36 | 0.00 | 0.00 | | | |
| Total | 5.19 | 94.81 | 29.34 | 41.10 | 15.77 |

PiONA (paraffins, isoparaffins, olefins, naphthenes, aromatics) composition of the fossil naphtha N1 used in the examples and in the comparative examples was determined by gas chromatography coupled to a flame ionization detector (GC-FID). The analysis results are shown in Table 6.

N1 comprised hydrocarbons in the range of carbon numbers C4-C7 approximately 99 wt-% of the total weight of N1. N1 comprised approximately 34 wt-% n-paraffins, approximately 40 wt-% i-paraffins, and approximately 25 wt-% mono naphthenes of the total weight of N1.

TABLE 6

Composition of fossil naphtha N1.

| Carbon Number | N1 | | |
|---|---|---|---|
| | nP | iP | Mono Naphthenes |
| 2 | 0.00 | 0.00 | 0.00 |
| 3 | 0.00 | 0.00 | 0.00 |
| 4 | 0.07 | 0.00 | 0.00 |
| 5 | 9.17 | 7.95 | 1.70 |
| 6 | 24.72 | 29.75 | 23.30 |
| 7 | 0.05 | 2.22 | 0.39 |
| 8 | 0.00 | 0.00 | 0.00 |
| 9 | 0.00 | 0.00 | 0.00 |
| >C10 | 0.00 | 0.00 | 0.00 |
| Total | 34.01 | 39.92 | 25.39 |

Two blends B1 and B2 of N1 and P1 and P2, respectively, were formed. For the comparative examples, a blend B3 of N1 and P3 was formed. The compositions of blends B1-B3 are shown in Table 7.

N1 comprised 250 ppm by weight sulfur. All renewable isomeric paraffin compositions P1-P3 were initially essentially free of sulfur and comprised sulfur less than 1 ppm by weight. When used as unblended steam cracking feedstock P1 and P2 were additised with dimethylsulfide (DMDS) to contain 250 ppm by weight sulfur, i.e. to match the sulfur content of N1. Blend B2 was also additised with DMDS to contain 250 ppm by weight sulfur. Unblended P3, and blends B1 and B3 were not additised. Consequently, unblended P3 was essentially free of sulfur, whereas the sulfur content of blends B1 and B3 originated from N1 and was 65.2 ppm by weight. Consequently, 250 ppm by weight sulfur was added to P1 and P2 respectively, and 187.5 ppm by weight sulfur was added to B2 which already comprised 65.2. ppm by weight sulfur originating from N1.

The DMDS was added to the feedstock in the steam. In other words, the addition of sulfur was performed by adding DMDS to steam and then injecting the steam to the steam cracking furnace (reactor coil 3) so that a sulfur content of 250 mg sulfur/kg feedstock was obtained The feedstocks and their sulfur contents are summarised in Table 7.

TABLE 7

Composition and sulfur content of blends B1, B2, and B3.

| Feedstock | Composition | | Sulfur (ppm by weight) |
|---|---|---|---|
| N1 (comparative) | 100 wt-% N1 | | 250 |
| P1 | 100 wt-% P1 | | 250 |
| P2 | 100 wt-% P2 | | 250 |
| P3 (comparative) | 100 wt-% P3 | | <1 |
| B1 | 75 wt-% P1 | 25 wt-% N1 | 62.5 |
| B2 | 75 wt-% P2 | 25 wt-% N1 | 250 |
| B3 (comparative) | 75 wt-% P3 | 25 wt-% N1 | 62.5 |

Steam cracking of the above described feedstocks was carried out at three different coil outlet temperatures (COTs), 800° C., 820° C., and 840° C. The flow rate ratio between water and the feedstock (dilution) was kept constant at 0.5 g H2O/g feedstock.

Table 8 shows the average wt-% amounts of impurities CO, $CO_2$, and $C_2H_2$ measured from the steam cracking effluent at the different coil outlet temperatures. The wt-% are based on the total weight of the steam cracking effluent. Total impurities is the sum of the wt-% amounts of CO, $CO_2$, and $C_2H_2$ (total amount of CO, $CO_2$, and $C_2H_2$).

TABLE 8

Average wt-% of impurities CO, $CO_2$, and $C_2H_2$ in steam cracking effluents obtained at the different COTs.

| Feedstock | CO | $CO_2$ | $C_2H_2$ | Total impurities |
|---|---|---|---|---|
| N1 (comparative) | 0.015 | 0.008 | 0.239 | 0.262 |
| P1 | 0.044 | 0.010 | 0.485 | 0.540 |
| P2 | 0.047 | 0.011 | 0.490 | 0.549 |
| P3 (comparative) | 0.061 | 0.010 | 0.593 | 0.664 |
| B1 | 0.057 | 0.011 | 0.507 | 0.575 |
| B2 | 0.049 | 0.011 | 0.594 | 0.655 |
| B3 (comparative) | 0.074 | 0.027 | 0.848 | 0.949 |

As can be seen from Table 8, surprisingly, the renewable isomeric paraffin compositions and the blends comprising renewable isomeric paraffin composition had a higher wt-% of total impurities compared to fossil naphtha. However, as further seen in Table 8, P1 and P2, as well as their blends B1 and B2, formed significantly less total impurities compared to P3 and its blend B3.

Combining fossil naphtha with renewable isomeric paraffin composition increased the production of CO and $CO_2$. This can be seen for example by comparing P1 and B1, as well as P3 and B3 in Table 8. It should be noted that the production of both CO and $CO_2$ increased significantly when P3 was blended with N1 (i.e. P3 compared to B3) despite the sulfur content of the feedstock increasing from less than 1 ppm by weight to 62.5 ppm by weight. In contrast, comparing P1 and B1 (Table 8) a much more subtle increase in the CO and $CO_2$ production was recorded despite the sulfur content of the feedstock decreasing from 250 ppm by weight to 62.5 ppm by weight. Additising the blend with DMDS contributed to decreasing the generation of CO and $CO_2$, as can be noticed by comparing P2 and B2 with P1 and B1 (Table 8). Overall, it can nevertheless be concluded that decreasing the ratio of the wt-% amount of isoparaffins with more than three branches to the total wt-% amount of isoparaffins in the renewable isomeric paraffin composition drastically decreases the formation of CO and especially $CO_2$. This effect can be demonstrated particularly by comparing B1 and B3 (Table 8) containing the same amount of sulfur. It can further be concluded that increasing the wt-% amount of isoparaffins in the range of carbon number C14-C18 in the renewable isomeric paraffin composition also contributes to the decrease in the formation of CO and $CO_2$.

As can be seen from Table 8, fossil naphtha surprisingly generated less $C_2H_2$ than the renewable isomeric paraffin composition or the blends comprising renewable isomeric paraffin composition. Surprisingly, the generation of $C_2H_2$ was increased when the renewable isomeric paraffin compositions were combined with fossil naphtha, respectively, as can be noted by comparing P1 with B1, P2 with B2, and P3 with B3 (Table 8). The sulfur content does not noteworthily influence the generation of $C_2H_2$ during steam cracking. As can be seen from Table 8, P2 generated slightly more $C_2H_2$ than P1. However, comparing P3 with P1 and P2 it can be seen that P3 generated significantly more $C_2H_2$ than either of P1 or P2 (Table 8). This is surprising considering the difference in the isomerisation degree between P2 and P3 (2.29 percentage points) and the difference in the isomerisation degree between P1 and P2 (23.48 percentage points). It can thus be concluded that the isomerisation degree is not a main factor in controlling the formation of $C_2H_2$. Similarly, as can be seen in Table 8, the increase in $C_2H_2$ generation between B1 and B2 was much more subtle than the increase in $C_2H_2$ generation between B3 and either B1 or B2, B1 generating less $C_2H_2$ than B2 or B3, and B2 generating less $C_2H_2$ than B3. It can thus be concluded that decreasing the ratio of the wt-% amount of isoparaffins with more than three branches to the total wt-% amount of isoparaffins in the renewable isomeric paraffin composition decreases the formation of $C_2H_2$. Further, increasing the wt-% amount of isoparaffins comprised in the range of carbon number C14-C18 in the renewable isomeric paraffin composition contributes to decreasing the formation of $C_2H_2$. Consequently, the wt-% of total impurities is also decreased by decreasing the ratio of the wt-% amount of isoparaffins with more than three branches to the total wt-% amount of isoparaffins in the renewable isomeric paraffin composition. This effect can be further enhanced by increasing the wt-% amount of isoparaffins comprised in the range of carbon number C14-C18 in the renewable isomeric paraffin composition.

Tables 9-12 show more detailed analysis results of the steam cracking effluents. As can be seen from Tables 11 and 12, performing the steam cracking at COTs 800° C. and 820° C. produced less CO and $CO_2$ compared to performing the steam cracking at COT 840° C. This was seen for all feedstocks of the examples, namely P1, P2, B1, and B2. Particularly low production of CO and $CO_2$ was obtained for all feedstocks of the examples (P1, P2, B1, and B2) at COT 800° C.

Surprisingly, COT 820° C. increased the formation of $C_2H_2$ when the feedstock was P1 or P2 compared to steam cracking the same feedstock at COTs 800° C. and 840° C. This effect was not seen when steam cracking blends B1 and B2. The production of $C_2H_2$ decreased with the COT when the feedstock was B1 or B2. The lowest $C_2H_2$ production was obtained at COT 800° C. for all feedstocks of the examples (P1, P2, B1, and B2). Accordingly, the production of impurities CO, $CO_2$, and $C_2H_2$ was further decreased at COT 800° C. When steam cracking blends of fossil naphtha and P1 or P2 a COT from the range 800-820° C. was shown to decrease the production of impurities CO, $CO_2$, and $C_2H_2$ compared to COT 840° C.

TABLE 9

Steam cracking effluent analysis, feedstocks N1 and P3 (comparative examples). The results are expressed in wt % based on the total weight of the effluent.

| Feedstock | N1 | N1 | N1 | P3 | P3 | P3 |
|---|---|---|---|---|---|---|
| Sulfur (ppm) | 250 | 250 | 250 | 250 | 250 | 250 |
| COT (° C.) | 800 | 820 | 840 | 800 | 820 | 840 |
| Dilution (gH2O/g feedstock) | 0.5 | 0.5 | 0.5 | 0.5 | 0.5 | 0.5 |
| CO | 0.013 | 0.015 | 0.032 | 0.035 | 0.054 | 0.092 |
| CO2 | 0.010 | 0.012 | 0.009 | 0.008 | 0.010 | 0.013 |
| C2H2 | 0.235 | 0.169 | 0.492 | 0.517 | 0.607 | 0.655 |
| H2 | 0.599 | 0.799 | 0.901 | 0.476 | 0.558 | 0.644 |
| Methane | 8.602 | 10.117 | 12.530 | 9.928 | 11.451 | 12.743 |
| Ethene | 19.353 | 23.063 | 27.942 | 26.624 | 28.912 | 30.518 |
| Propene | 16.254 | 17.955 | 17.174 | 19.730 | 19.401 | 18.430 |
| 1,3-butadiene | 3.573 | 4.423 | 4.964 | 6.410 | 6.833 | 6.808 |
| non-aromatic C5-C9 | 36.733 | 24.735 | 17.024 | 14.622 | 8.228 | 4.678 |
| Benzene | 2.338 | 5.217 | 5.816 | 3.258 | 6.883 | 9.195 |
| Toluene | 0.261 | 0.803 | 1.190 | 1.949 | 2.684 | 3.538 |
| Xylenes | 0.101 | 0.000 | 0.118 | 0.093 | 0.133 | 0.082 |
| others | 11.928 | 12.691 | 11.810 | 16.348 | 14.247 | 12.605 |
| BTX (benzene, toluene, xylenes) | 2.699 | 6.020 | 7.124 | 5.301 | 9.699 | 12.815 |
| Ethene and Propene | 35.607 | 41.018 | 45.116 | 46.354 | 48.313 | 48.948 |
| HVC (ethene, propene, 1,3-butadiene, and BTX) | 41.879 | 51.461 | 57.203 | 58.065 | 64.846 | 68.571 |
| Total Impurities (CO, CO2, and C2H2) | 0.259 | 0.196 | 0.533 | 0.560 | 0.671 | 0.760 |
| Total Sum of All Species | 100.00 | 100.00 | 100.00 | 100.00 | 100.00 | 100.00 |

TABLE 10

Steam cracking effluent analysis, feedstock B3 (comparative examples). The results are expressed in wt-% based on the total weight of the effluent.

| Feedstock | B3 | B3 | B3 |
|---|---|---|---|
| Sulfur (ppm) | 62.5 | 62.5 | 62.5 |
| COT (° C.) | 800 | 820 | 840 |
| Dilution (g H2O/g feedstock) | 0.5 | 0.5 | 0.5 |
| CO | 0.042 | 0.073 | 0.107 |
| CO2 | 0.025 | 0.025 | 0.031 |
| C2H2 | 1.149 | 0.654 | 0.741 |
| H2 | 0.490 | 0.651 | 0.709 |
| Methane | 8.964 | 11.185 | 11.858 |
| Ethene | 23.573 | 29.121 | 30.289 |
| Propene | 18.260 | 19.511 | 18.468 |
| 1,3-butadiene | 5.463 | 6.389 | 6.595 |
| non-aromatic C5-C9 | 19.625 | 10.231 | 7.692 |
| Benzene | 3.930 | 6.492 | 8.084 |
| Toluene | 1.141 | 1.910 | 2.696 |
| Xylenes | 0.181 | 0.097 | 0.153 |
| others | 17.156 | 13.660 | 12.576 |
| BTX (benzene, toluene, xylenes) | 5.252 | 8.499 | 10.933 |
| Ethene and Propene | 41.833 | 48.633 | 48.757 |
| HVC (ethene, propene, 1,3-butadiene, and BTX) | 52.549 | 63.521 | 66.286 |
| Total Impurities (CO, CO2, and C2H2) | 1.216 | 0.752 | 0.879 |
| Total Sum of All Species | 100.00 | 100.00 | 100.00 |

TABLE 11

Steam cracking effluent analysis, feedstocks P1 and P2. The results are expressed in wt % based on the total weight of the effluent.

| Feedstock | P1 | P1 | P1 | P2 | P2 | P2 |
|---|---|---|---|---|---|---|
| Sulfur (ppm) | 250 | 250 | 250 | 250 | 250 | 250 |
| COT (° C.) | 800 | 820 | 840 | 800 | 820 | 840 |
| Dilution (gH2O/gHC) | 0.5 | 0.5 | 0.5 | 0.5 | 0.5 | 0.5 |
| CO | 0.022 | 0.046 | 0.065 | 0.031 | 0.047 | 0.064 |
| CO2 | 0.006 | 0.011 | 0.014 | 0.009 | 0.010 | 0.015 |
| C2H2 | 0.190 | 0.696 | 0.570 | 0.387 | 0.611 | 0.474 |
| H2 | 0.396 | 0.504 | 0.596 | 0.449 | 0.538 | 0.604 |
| Methane | 7.989 | 9.751 | 11.004 | 9.375 | 10.797 | 11.739 |
| Ethene | 28.219 | 32.745 | 34.348 | 27.653 | 29.559 | 30.226 |
| Propene | 17.009 | 18.098 | 17.188 | 19.216 | 18.668 | 17.304 |
| 1,3-butadiene | 5.725 | 6.786 | 6.768 | 6.472 | 6.683 | 6.513 |
| non-aromatic C5-C9 | 8.890 | 10.256 | 9.937 | 12.528 | 9.786 | 9.782 |
| Benzene | 2.757 | 3.840 | 6.452 | 4.783 | 6.688 | 7.172 |

TABLE 11-continued

Steam cracking effluent analysis, feedstocks P1 and P2. The results are expressed in wt % based on the total weight of the effluent.

| Feedstock | P1 | P1 | P1 | P2 | P2 | P2 |
|---|---|---|---|---|---|---|
| Toluene | 0.940 | 1.404 | 2.034 | 1.948 | 2.730 | 2.582 |
| Xylenes | 0.475 | 0.082 | 0.228 | 0.169 | 0.246 | 0.122 |
| others | 27.383 | 15.781 | 10.795 | 16.980 | 13.637 | 13.403 |
| BTX (benzene, toluene, xylenes) | 4.172 | 5.326 | 8.714 | 6.900 | 9.664 | 9.876 |
| Ethene and Propene | 45.228 | 50.844 | 51.536 | 46.869 | 48.227 | 47.531 |
| HVC (ethene, propene, 1,3-butadiene, and BTX) | 55.125 | 62.956 | 67.019 | 60.241 | 64.574 | 63.919 |
| Total Impurities (CO, CO2, and C2H2) | 0.218 | 0.752 | 0.649 | 0.427 | 0.668 | 0.553 |
| Total Sum of All Species | 100.00 | 100.00 | 100.00 | 100.00 | 100.00 | 100.00 |

TABLE 12

Steam cracking effluent analysis, feedstocks B1 and B2. The results are expressed in wt % based on the total weight of the effluent.

| Feedstock | B1 | B1 | B1 | B2 | B2 | B2 |
|---|---|---|---|---|---|---|
| Sulfur (ppm) | 62.5 | 62.5 | 62.5 | 250 | 250 | 250 |
| COT (° C.) | 800 | 820 | 840 | 800 | 820 | 840 |
| Dilution (g H2O/g feedstock) | 0.5 | 0.5 | 0.5 | 0.5 | 0.5 | 0.5 |
| CO | 0.027 | 0.047 | 0.097 | 0.036 | 0.038 | 0.073 |
| CO2 | 0.007 | 0.010 | 0.017 | 0.014 | 0.008 | 0.011 |
| C2H2 | 0.314 | 0.298 | 0.909 | 0.402 | 0.630 | 0.751 |
| H2 | 0.454 | 0.562 | 0.653 | 0.522 | 0.589 | 0.679 |
| Methane | 7.712 | 9.241 | 10.189 | 9.175 | 10.463 | 11.201 |
| Ethene | 27.035 | 31.519 | 33.728 | 27.058 | 27.777 | 30.563 |
| Propene | 17.537 | 18.349 | 17.729 | 18.855 | 17.796 | 17.694 |
| 1,3-butadiene | 5.589 | 6.388 | 6.638 | 5.977 | 6.111 | 6.313 |
| non-aromatic C5-C9 | 15.081 | 15.582 | 12.825 | 20.136 | 14.722 | 10.847 |
| Benzene | 4.332 | 5.953 | 6.094 | 4.426 | 5.958 | 7.849 |
| Toluene | 1.217 | 1.321 | 1.172 | 1.294 | 1.891 | 2.088 |
| Xylenes | 0.135 | 0.081 | 0.076 | 0.141 | 0.184 | 0.161 |
| others | 19.355 | 10.650 | 10.882 | 15.613 | 13.832 | 11.771 |
| BTX (benzene, toluene, xylenes) | 5.684 | 7.355 | 7.342 | 5.860 | 8.033 | 10.097 |
| Ethene and Propene | 44.572 | 49.868 | 51.457 | 45.913 | 45.573 | 48.257 |
| HVC (ethene, propene, 1,3-butadiene, and BTX) | 55.845 | 63.611 | 65.436 | 57.751 | 59.717 | 64.667 |
| Total Impurities (CO, CO2, and C2H2) | 0.348 | 0.354 | 1.023 | 0.453 | 0.677 | 0.834 |
| Total Sum of All Species | 98.79 | 100.00 | 101.01 | 103.65 | 100.00 | 100.00 |

Implementation and embodiments of the present invention are further discussed in the following clauses:

(1) A method comprising the steps of a) providing a thermal cracking feedstock comprising 1-100 wt-% renewable isomeric paraffin composition of the total weight of the thermal cracking feedstock, the renewable isomeric paraffin composition comprising at least 60 wt-% paraffins of the total weight of the renewable isomeric paraffin composition, wherein of said paraffins 10-95 wt-% are isoparaffins, and the ratio of the wt-% amount of isoparaffins with more than three branches to the total wt-% amount of the isoparaffins is less than 0.15, and 0-99 wt-% fossil naphtha of the total weight of the thermal cracking feedstock, the sum of the wt-% amounts of the renewable isomeric paraffin composition and of the fossil naphtha being at least 90 wt-% of the total weight of the thermal cracking feedstock; and b) thermally cracking the thermal cracking feedstock provided in step a) to form a cracking product comprising a mixture of hydrocarbons.

(2) The method according to clause 1, wherein the thermal cracking feedstock comprises 50-100 wt-% renewable isomeric paraffin composition of the total weight of the thermal cracking feedstock, and 0-50 wt-% fossil naphtha of the total weight of the thermal cracking feedstock.

(3) The method according to any of the preceding clauses, wherein the thermal cracking feedstock comprises 50-85 wt-% renewable isomeric paraffin composition and 15-50 wt-% fossil naphtha, preferably 60-85 wt-% renewable isomeric paraffin composition and 15-40 wt-% fossil naphtha, more preferably 70-85 wt-% renewable isomeric paraffin composition and 15-30 wt-% fossil naphtha, of the total weight of the thermal cracking feedstock, the sum of the wt-% amounts of the renewable isomeric paraffin composition and of the fossil naphtha preferably being at least 95 wt-%, more preferably at least 99 wt-%, of the total weight of the thermal cracking feedstock.

(4) The method according to any of the preceding clauses, wherein the ratio of the wt-% amount of isoparaffins with more than three branches to the total wt-% amount of the isoparaffins in the renewable isomeric paraffin composition is less than 0.12, preferably less than 0.10, more preferably less than 0.05.

(5) The method according to any of the preceding clauses, wherein of the isoparaffins in the renewable isomeric paraffin composition at least 80 wt-%, preferably at least 85 wt-%, more preferably at least 90 wt-%, even more preferably at least 95 wt-% are in the range of carbon number C14-C18.

(6) The method according to any of the preceding clauses, wherein of the paraffins in the renewable isomeric paraffin composition 60-95 wt-%, preferably 60-80 wt-%, further preferably 65-70 wt-% are isoparaffins, the renewable isomeric paraffin composition comprising paraffins preferably at least 70 wt-%, further preferably at least 80 wt-%, more preferably at least 90 wt-%, even more preferably at least 95 wt-%, of the total weight of the renewable isomeric paraffin composition.

(7) The method according to any of the preceding clauses, wherein the fossil naphtha comprises 20-85 wt-% paraffins, 0-35 wt-% olefins, 10-30 wt-% naphthenes, and 0-30 wt-% aromatics of the total weight of the fossil naphtha, the wt-% of hydrocarbons in the fossil naphtha preferably being at least 95 wt-%, more preferably at least 99 wt-% of the total weight of the fossil naphtha.

(8) The method according to any of the preceding clauses, wherein the thermal cracking feedstock comprises sulfur 20-300 ppm by weight, preferably 20-250 ppm by weight, more preferably 20-100 ppm by weight, and even more preferably 50-65 ppm by weight.

(9) The method according to any of the preceding clauses, wherein step b) is conducted at a coil outlet temperature (COT) selected from the range from 780° C. to 890° C., preferably from 800° C. to 860° C., more preferably from 800° C. to 840° C., and even more preferably from 800° C. to 820° C.

(10) The method according to any of the preceding clauses comprising the step of c) subjecting at least a portion of the cracking product formed in step b) to a purification treatment to remove at least one of CO, $CO_2$, or $C_2H_2$.

(11) The method according to any of the preceding clauses comprising) the step of d) subjecting at least a portion of the cracking product formed in step b), or at least a portion of the cracking product subjected to the purification treatment of step c), or both, to a polymerisation treatment to produce polymers.

(12) The method according to any of the preceding clauses, comprising providing multiple thermal cracker furnaces, and performing step b) in at least one of the multiple thermal cracker furnaces.

(13) The method according to clause 12, comprising obtaining cracking products from the multiple thermal cracking furnaces, and mixing the obtained cracking products to form a combined cracking product, and optionally subjecting at least a portion of the combined cracking product to a purification treatment to remove at least one of CO, $CO_2$, or $C_2H_2$, or to a polymerisation treatment to form polymers, or to both the purification treatment and the polymerisation treatment.

(14) A thermal cracking feedstock comprising 1-100 wt-% renewable isomeric paraffin composition of the total weight of the thermal cracking feedstock, the renewable isomeric paraffin composition comprising at least 60 wt-% paraffins of the total weight of the renewable isomeric paraffin composition, wherein of said paraffins 10-95 wt-% are isoparaffins, and the ratio of the wt-% amount of isoparaffins with more than three branches to the total wt-% amount of the isoparaffins is less than 0.15, and 0-99 wt-% fossil naphtha of the total weight of the thermal cracking feedstock, the sum of the wt-% amounts of the renewable isomeric paraffin composition and of the fossil naphtha being at least 90 wt-% of the total weight of the thermal cracking feedstock.

(15) The thermal cracking feedstock according to clause 14, wherein the thermal cracking feedstock comprises 50-100 wt-% renewable isomeric paraffin composition of the total weight of the thermal cracking feedstock, and 0-50 wt-% fossil naphtha of the total weight of the thermal cracking feedstock.

(16) The thermal cracking feedstock according to clause 14 or 15, wherein the thermal cracking feedstock comprises 50-85 wt-% renewable isomeric paraffin composition and 15-50 wt-% fossil naphtha, preferably 60-85 wt-% renewable isomeric paraffin composition and 15-40 wt-% fossil naphtha, more preferably 70-85 wt-% renewable isomeric paraffin composition and 15-30 wt-% fossil naphtha of the total weight of the thermal cracking feedstock, the sum of the wt-% amounts of the renewable isomeric paraffin composition and of the fossil naphtha being preferably at least 95 wt-%, more preferably at least 99 wt-%, of the total weight of the thermal cracking feedstock.

(17) The thermal cracking feedstock according to any of the preceding clauses 14 to 16, wherein the ratio of the wt-% amount of isoparaffins with more than three branches to the total wt-% amount of the isoparaffins in the renewable isomeric paraffin composition is less than 0.12, preferably less than 0.10, more preferably less than 0.05.

(18) The thermal cracking feedstock according to any of the preceding clauses 14 to 17, wherein of the isoparaffins in the renewable isomeric paraffin composition at least 80 wt-%, preferably at least 85 wt-%, more preferably at least 90 wt-%, even more preferably at least 95 wt-%, are in the range of carbon number C14-C18.

(19) The thermal cracking feedstock according to any of the preceding clauses 14 to 18, wherein of the paraffins in the renewable isomeric paraffin composition 60-95 wt-%, preferably 60-80 wt-%, further preferably 65-70 wt-% are isoparaffins, the renewable isomeric paraffin composition comprising paraffins preferably at least 70 wt-%, further preferably at least 80 wt-%, more preferably at least 90 wt-%, even more preferably at least 99 wt-%, of the total weight of the renewable isomeric paraffin composition.

(20) The thermal cracking feedstock according to any of the preceding clauses 14 to 19, wherein the fossil naphtha comprises 20-85 wt-% paraffins, 0-35 wt-% olefins, 10-30 wt-% naphthenes, and 0-30 wt-% aromatics of the total weight of the fossil naphtha, the wt-% of hydrocarbons in the fossil naphtha preferably being at least 95 wt-%, more preferably at least 99 wt-%, of the total weight of the fossil naphtha.

(21) The thermal cracking feedstock according to any of the preceding clauses 14 to 20, wherein the thermal cracking feedstock comprises sulfur 20-300 ppm by weight, preferably 20-250 ppm by weight, more preferably 20-100 ppm by weight, and most preferably 50-65 ppm by weight.

(22) A cracking product comprising a mixture of hydrocarbons obtainable by a method according to any of the preceding clauses 1-13, wherein the sum of the wt-% amounts of CO, $CO_2$ and $C_2H_2$ in the cracking product is less than 1.5 wt-%, preferably less than 1.3 wt-%, more preferably less than 1.1 wt-%, even more preferably less than 0.8 wt-%, of the total weight of the cracking product.

(23) Use of the cracking product according to clause 22 for producing polymers, such as polypropene, polyethene, or both.

(24) An article of manufacture comprising polymers obtainable by a method according to clause 11 or clause 13.

The foregoing description has provided by way of non-limiting examples of particular implementations and embodiments of the invention a full and informative description of the best mode presently contemplated by the inventors for carrying out the invention. It is however clear to a person skilled in the art that the invention is not restricted to details of the embodiments presented in the foregoing, but that it can be implemented in other embodiments using equivalent means or in different combinations of embodiments without deviating from the characteristics of the invention.

Furthermore, some of the features of the afore-disclosed embodiments of this invention may be used to advantage without the corresponding use of other features. As such, the foregoing description shall be considered as merely illustrative of the principles of the present invention, and not in limitation thereof. Hence, the scope of the invention is only restricted by the appended patent claims.

What is claimed is:

1. A thermal cracking feedstock, comprising:
   a 1-100 wt-% renewable isomeric paraffin composition of a total weight of a thermal cracking feedstock, the renewable isomeric paraffin composition containing:
   at least 60 wt-% paraffins of a total weight of the renewable isomeric paraffin composition, wherein of said paraffins 10-95 wt-% are isoparaffins and of said isoparaffins at least 80 wt-% are in a range of carbon number C14-C18, and a ratio of a wt-% amount of isoparaffins with more than three branches to a total wt-% amount of the isoparaffins is less than 0.12; and
   0-99 wt-% fossil naphtha of the total weight of the thermal cracking feedstock,
   a sum of wt-% amounts of the renewable isomeric paraffin composition and of the fossil naphtha is at least 90 wt-% of the total weight of the thermal cracking feedstock.

2. The thermal cracking feedstock according to claim 1, wherein the thermal cracking feedstock comprises:
   50-100 wt-% renewable isomeric paraffin composition of the total weight of the thermal cracking feedstock; and
   0-50 wt-% fossil naphtha of the total weight of the thermal cracking feedstock.

3. The thermal cracking feedstock according to claim 2, wherein the ratio of the wt-% amount of isoparaffins with more than three branches to the total wt-% amount of the isoparaffins in the renewable isomeric paraffin composition is less than 0.10.

4. The thermal cracking feedstock according to claim 3, wherein of the isoparaffins in the renewable isomeric paraffin composition, at least 85 wt-% are in the range of carbon number C14-C18.

5. The thermal cracking feedstock according to claim 4, wherein of the total weight of the renewable isomeric paraffin composition at least 70 wt-% are paraffins, and of the paraffins in the renewable isomeric paraffin composition, 60-95 wt-%, are isoparaffins.

6. The thermal cracking feedstock according to claim 5, wherein the fossil naphtha comprises:
   20-85 wt-% paraffins, 0-35 wt-% olefins, 10-30 wt-% naphthenes, and 0-30 wt-% aromatics of a total weight of the fossil naphtha, a wt-% of hydrocarbons in the fossil naphtha is at least 95 wt-% of a total weight of the fossil naphtha.

7. The thermal cracking feedstock according to claim 6, wherein the thermal cracking feedstock comprises:
   sulfur 20-300 ppm by weight.

8. The thermal cracking feedstock according to claim 1, wherein the thermal cracking feedstock comprises:
   50-85 wt-% renewable isomeric paraffin composition and 15-50 wt-% fossil naphtha of the total weight of the thermal cracking feedstock; and
   the sum of the wt-% amounts of the renewable isomeric paraffin composition and of the fossil naphtha is at least 95 wt % of the total weight of the thermal cracking feedstock.

9. The thermal cracking feedstock according to claim 8, wherein of the isoparaffins in the renewable isomeric paraffin composition, at least 85 wt-% are in the range of carbon number C14-C18.

10. The thermal cracking feedstock according to claim 8, wherein the thermal cracking feedstock comprises:
    50-85 wt-% renewable isomeric paraffin composition and 15-50 wt-% fossil naphtha of the total weight of the thermal cracking feedstock; and
    the sum of the wt-% amounts of the renewable isomeric paraffin composition and of the fossil naphtha is at least 99 wt-% of the total weight of the thermal cracking feedstock.

11. The thermal cracking feedstock according to claim 1, wherein the ratio of the wt-% amount of isoparaffins with more than three branches to the total wt-% amount of the isoparaffins in the renewable isomeric paraffin composition is less than 0.10.

12. The thermal cracking feedstock according to claim 11, wherein the ratio of the wt-% amount of isoparaffins with more than three branches to the total wt-% amount of the isoparaffins in the renewable isomeric paraffin composition is less than 0.05.

13. The thermal cracking feedstock according to claim 1, wherein of the isoparaffins in the renewable isomeric paraffin composition, at least 85 wt % are in the range of carbon number C14-C18.

14. The thermal cracking feedstock according to claim 13, wherein of the isoparaffins in the renewable isomeric paraffin composition, at least 95 wt-% are in the range of carbon number C14-C18.

15. The thermal cracking feedstock according to claim 1, wherein of the total weight of the renewable isomeric paraffin composition at least 70 wt % are paraffins, and of the paraffins in the renewable isomeric paraffin composition, 60-95 wt % are isoparaffins.

16. The thermal cracking feedstock according to claim 15, wherein of the total weight of the renewable isomeric paraffin composition at least 80 wt-% are paraffins.

17. The thermal cracking feedstock according to claim 15, wherein of the paraffins in the renewable isomeric paraffin composition, 60-80 wt-% are isoparaffins.

18. The thermal cracking feedstock according to claim 1, wherein the fossil naphtha comprises:
   20-85 wt-% paraffins, 0-35 wt-% olefins, 10-30 wt-% naphthenes, and 0-30 wt-% aromatics of a total weight of the fossil naphtha, a wt-% of hydrocarbons in the fossil naphtha is at least 95 wt % of a total weight of the fossil naphtha.

19. The thermal cracking feedstock according to claim 1, wherein the thermal cracking feedstock comprises:
   sulfur 20-300 ppm by weight.

20. The thermal cracking feedstock according to claim 19, wherein the thermal cracking feedstock comprises:
   sulfur 20-250 ppm by weight.

21. The thermal cracking feedstock according to claim 19, wherein the thermal cracking feedstock comprises:
   sulfur 20-100 ppm by weight.

22. The thermal cracking feedstock according to claim 19, wherein the thermal cracking feedstock comprises:
   sulfur 50-65 ppm by weight.

23. The thermal cracking feedstock according to claim 1, wherein the thermal cracking feedstock comprises:
   60-85 wt-% renewable isomeric paraffin composition and 15-40 wt-% fossil naphtha of the total weight of the thermal cracking feedstock; and
   the sum of the wt-% amounts of the renewable isomeric paraffin composition and of the fossil naphtha is at least 95 wt-% of the total weight of the thermal cracking feedstock.

24. The thermal cracking feedstock according to claim 1, wherein of the isoparaffins in the renewable isomeric paraffin composition, at least 90 wt-% are in the range of carbon number C14-C18.

* * * * *